US012678638B2

(12) United States Patent
Rezai et al.

(10) Patent No.: US 12,678,638 B2
(45) Date of Patent: Jul. 14, 2026

(54) TARGETED NEUROMODULATION TO IMPROVE NEUROPSYCHIATRIC FUNCTION

(71) Applicant: West Virginia University Board of Governors on behalf of West Virginia University, Morgantown, WV (US)

(72) Inventors: Ali Rezai, Morgantown, WV (US); Victor Finomore, Morgantown, WV (US); Pierre D'Haese, Morgantown, WV (US)

(73) Assignee: West Virginia University Board of Governors on behalf of West Virginia University, Morgantown, WV (US)

( * ) Notice: Subject to any disclaimer, the term of this patent is extended or adjusted under 35 U.S.C. 154(b) by 0 days.

(21) Appl. No.: 18/238,446

(22) Filed: Aug. 25, 2023

(65) Prior Publication Data

US 2024/0075320 A1     Mar. 7, 2024

Related U.S. Application Data

(63) Continuation-in-part of application No. 18/310,465, filed on May 1, 2023, and a continuation-in-part of application No. 18/227,270, filed on Jul. 27, 2023.

(Continued)

(51) Int. Cl.
*A61N 7/00* (2006.01)
*A61N 1/36* (2006.01)

(52) U.S. Cl.
CPC ........... *A61N 7/00* (2013.01); *A61N 1/36082* (2013.01); *A61N 2007/0026* (2013.01)

(58) Field of Classification Search
CPC .................. A61N 7/00; A61N 1/36082; A61N 2007/0026
See application file for complete search history.

(56) References Cited

U.S. PATENT DOCUMENTS

2015/0119689 A1*  4/2015  Pascual-Leone ...... A61N 2/006
                                                    600/407
2015/0272468 A1*  10/2015  Liu ..................... A61B 5/0042
                                                    600/410

(Continued)

FOREIGN PATENT DOCUMENTS

JP       2017500911 A     1/2017
WO       2013172981 A1   11/2013
WO       2015073411 A1    5/2015

OTHER PUBLICATIONS

Zhai, Zhaolin, et al. "The efficacy of low-intensity transcranial ultrasound stimulation on negative symptoms in schizophrenia: a double-blind, randomized sham-controlled study." Brain Stimulation: Basic, Translational, and Clinical Research in Neuromodulation 16.3 (2023): 790-792.

(Continued)

*Primary Examiner* — Hien N Nguyen
(74) *Attorney, Agent, or Firm* — Tarolli, Sundheim, Covell & Tummino LLP

(57) ABSTRACT

Systems and methods are provided for targeting neuromodulation. A first image, representing a structure of the brain, is acquired from a first imaging system and a second image, representing a connectivity of the brain, is acquired from either the first imaging system or a second imaging system. A first utility value associated with directly modulating tissue within a region of interest is determined for each of a plurality of voxels within the region of interest from the first image. A second utility value associated with indirectly modulating tissue outside of the region of interest by modulating tissue within the region of interest is determined for each of the plurality of voxels from the second image. An overall utility value for each of the plurality of voxels is determined from the first utility value and the second utility (Continued)

value, and an optimal location is determined from the overall utility values.

21 Claims, 7 Drawing Sheets

Related U.S. Application Data

(60) Provisional application No. 63/400,960, filed on Aug. 25, 2022.

(56) References Cited

U.S. PATENT DOCUMENTS

| | | | | |
|---|---|---|---|---|
| 2020/0114161 A1* | 4/2020 | Fox | ...................... | A61B 5/7267 |
| 2022/0110694 A1* | 4/2022 | Williams | ............. | A61B 5/0036 |
| 2023/0419484 A1* | 12/2023 | Moreno | ................. | G16H 20/40 |

OTHER PUBLICATIONS

Wang, Yao, et al. "The effects and mechanisms of transcranial ultrasound stimulation combined with cognitive rehabilitation on post-stroke cognitive impairment." Neurological Sciences 43.7 (2022): 4315-4321.

Shimokawa, Hiroaki, et al. "A pilot study of whole-brain low-intensity pulsed ultrasound therapy for early stage of Alzheimer's disease (LIPUS-AD): A randomized, double-blind, placebo-controlled trial." The Tohoku Journal of Experimental Medicine 258.3 (2022): 167-175.

Samuel, Nardin, et al. "Accelerated transcranial ultrasound neuromodulation in Parkinson's disease: a pilot study." Movement Disorders 38.12 (2023): 2209-2216.

Riis, Thomas, et al. "Device for multifocal delivery of ultrasound into deep brain regions in humans." IEEE Transactions on Biomedical Engineering (2023).

Riis, Thomas S., et al. "Durable effects of deep brain ultrasonic neuromodulation on major depression: a case report." Journal of Medical Case Reports 17.1 (2023): 449.

Reznik, Samantha J., et al. "A double-blind pilot study of transcranial ultrasound (TUS) as a five-day intervention: TUS mitigates worry among depressed participants." Neurology, Psychiatry and Brain Research 37 (2020): 60-66.

Nicodemus, Natalie Eleanor, et al. "Focused transcranial ultrasound for treatment of neurodegenerative dementia." Alzheimer's & Dementia: Translational Research & Clinical Interventions 5 (2019): 374-381.

Mahdavi, Kennedy D., et al. "A pilot study of low-intensity focused ultrasound for treatment-resistant generalized anxiety disorder." Journal of Psychiatric Research 168 (2023): 125-132.

Jeong, Hyeonseok, et al. "Short-term efficacy of transcranial focused ultrasound to the hippocampus in Alzheimer's disease: A preliminary study." Journal of Personalized Medicine 12.2 (2022): 250.

Lee, Kyuheon, et al. "A review of functional neuromodulation in humans using low-intensity transcranial focused ultrasound." Biomedical Engineering Letters (2024): 1-32.

Corresponding European Patent Application No. 23776146.5, Communication pursuant to Article 94(3) EPC, dated Jan. 28, 2026.

Corresponding Japanese Patent Application No. 2025-511975, First Office Action, dated Apr. 21, 2026.

* cited by examiner

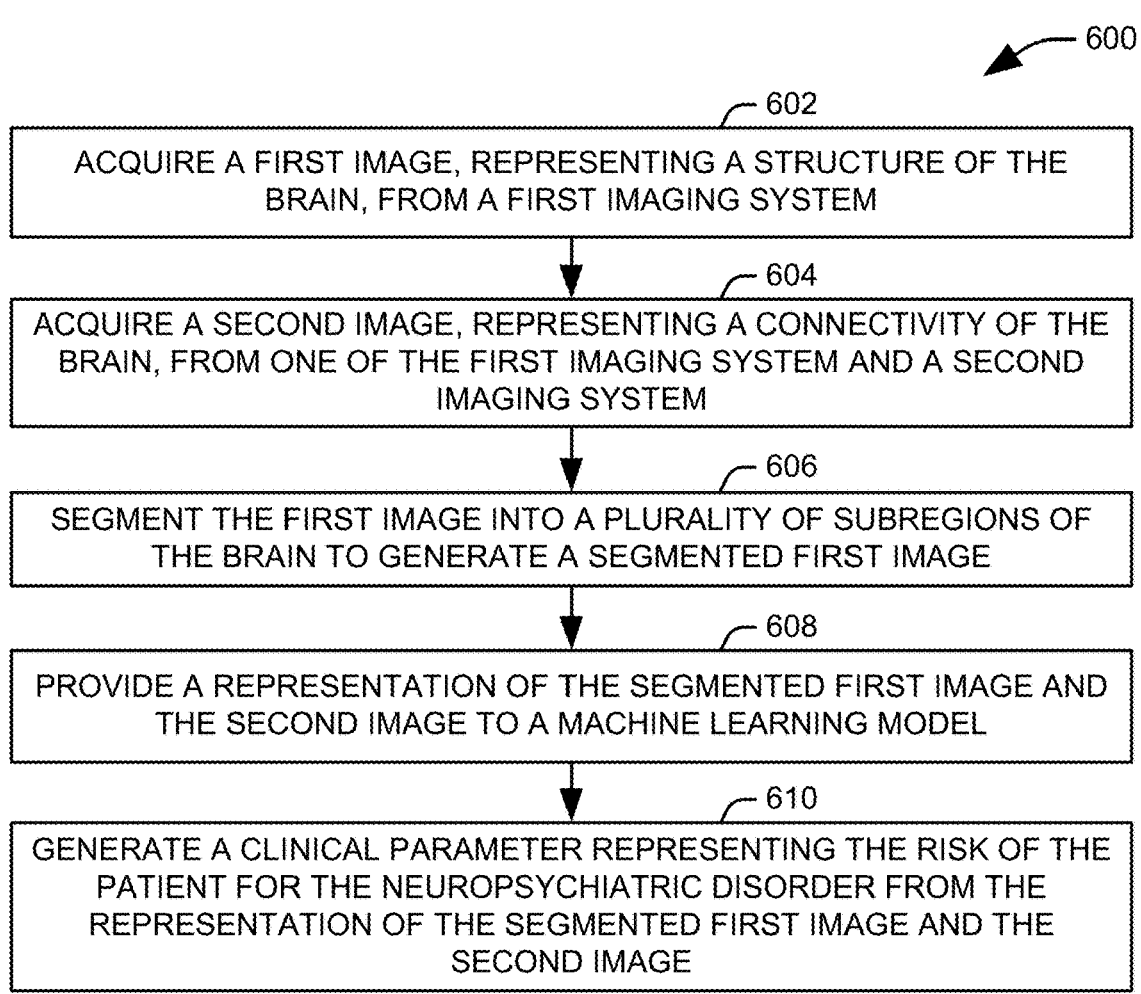

600

602

ACQUIRE A FIRST IMAGE, REPRESENTING A STRUCTURE OF THE BRAIN, FROM A FIRST IMAGING SYSTEM

604

ACQUIRE A SECOND IMAGE, REPRESENTING A CONNECTIVITY OF THE BRAIN, FROM ONE OF THE FIRST IMAGING SYSTEM AND A SECOND IMAGING SYSTEM

606

SEGMENT THE FIRST IMAGE INTO A PLURALITY OF SUBREGIONS OF THE BRAIN TO GENERATE A SEGMENTED FIRST IMAGE

608

PROVIDE A REPRESENTATION OF THE SEGMENTED FIRST IMAGE AND THE SECOND IMAGE TO A MACHINE LEARNING MODEL

610

GENERATE A CLINICAL PARAMETER REPRESENTING THE RISK OF THE PATIENT FOR THE NEUROPSYCHIATRIC DISORDER FROM THE REPRESENTATION OF THE SEGMENTED FIRST IMAGE AND THE SECOND IMAGE

FIG. 6

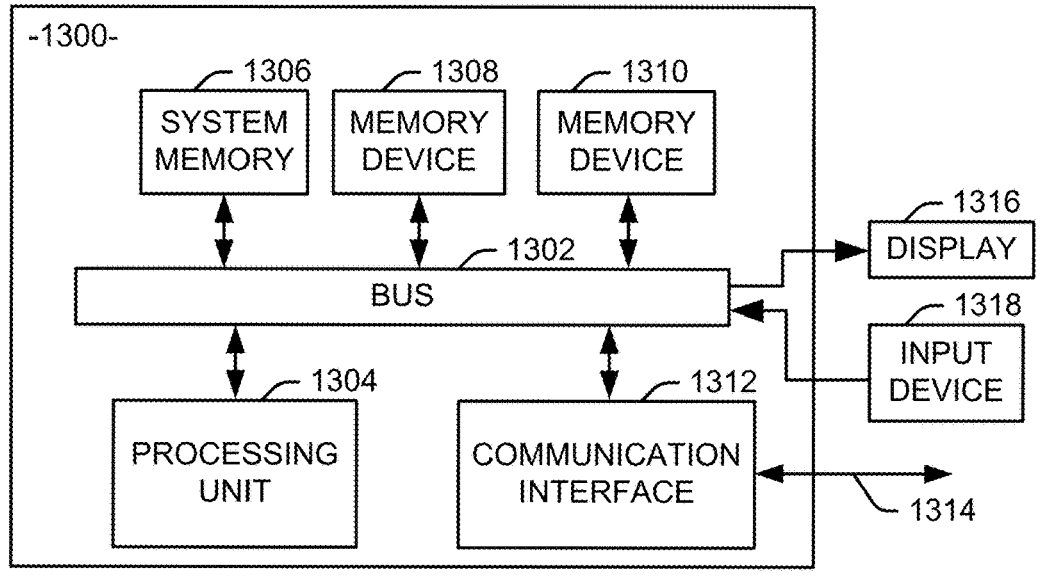

-1300-

1306
SYSTEM MEMORY

1308
MEMORY DEVICE

1310
MEMORY DEVICE

1316
DISPLAY

1302
BUS

1318
INPUT DEVICE

1304
PROCESSING UNIT

1312
COMMUNICATION INTERFACE

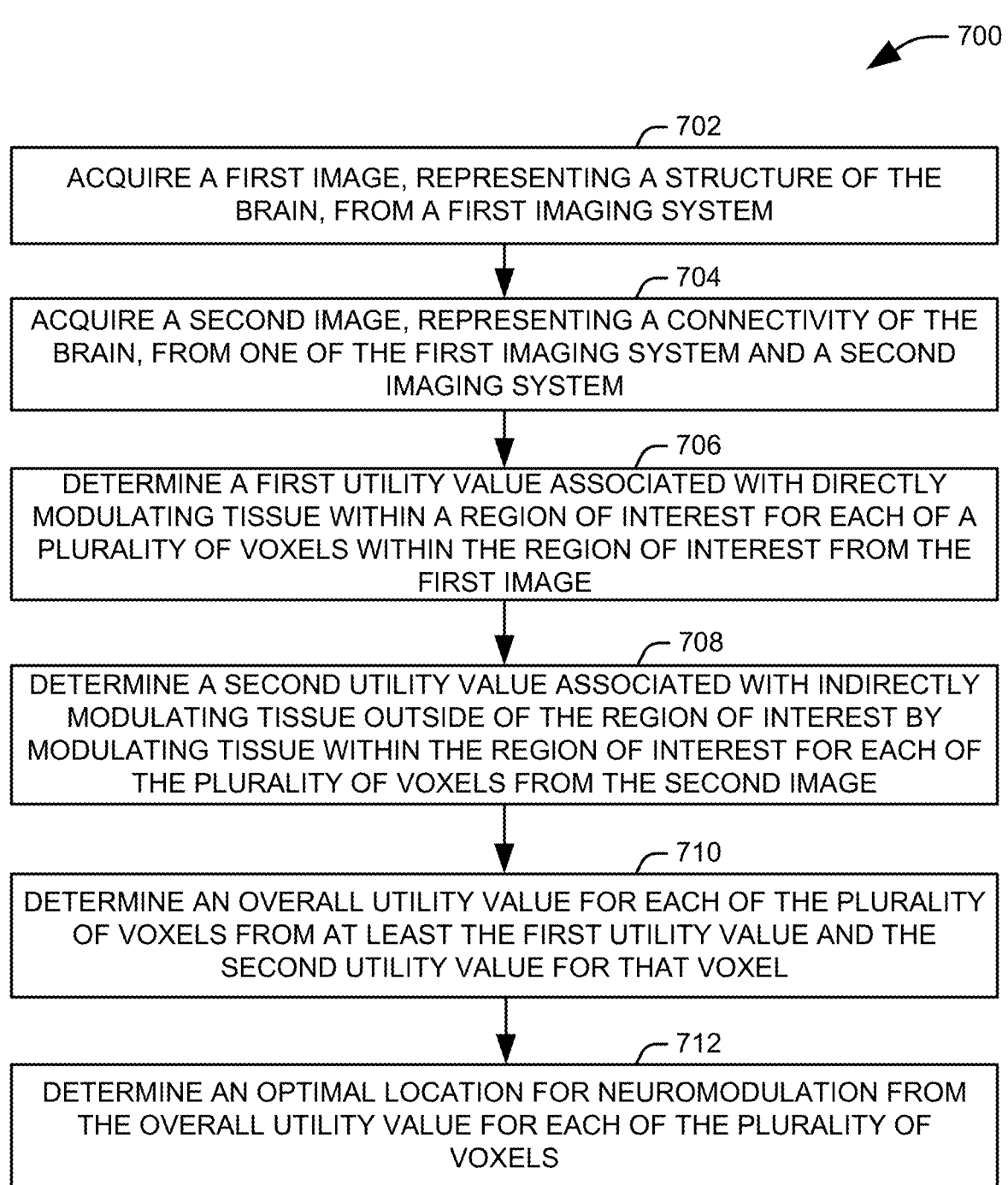

700

702

ACQUIRE A FIRST IMAGE, REPRESENTING A STRUCTURE OF THE BRAIN, FROM A FIRST IMAGING SYSTEM

704

ACQUIRE A SECOND IMAGE, REPRESENTING A CONNECTIVITY OF THE BRAIN, FROM ONE OF THE FIRST IMAGING SYSTEM AND A SECOND IMAGING SYSTEM

706

DETERMINE A FIRST UTILITY VALUE ASSOCIATED WITH DIRECTLY MODULATING TISSUE WITHIN A REGION OF INTEREST FOR EACH OF A PLURALITY OF VOXELS WITHIN THE REGION OF INTEREST FROM THE FIRST IMAGE

708

DETERMINE A SECOND UTILITY VALUE ASSOCIATED WITH INDIRECTLY MODULATING TISSUE OUTSIDE OF THE REGION OF INTEREST BY MODULATING TISSUE WITHIN THE REGION OF INTEREST FOR EACH OF THE PLURALITY OF VOXELS FROM THE SECOND IMAGE

710

DETERMINE AN OVERALL UTILITY VALUE FOR EACH OF THE PLURALITY OF VOXELS FROM AT LEAST THE FIRST UTILITY VALUE AND THE SECOND UTILITY VALUE FOR THAT VOXEL

712

DETERMINE AN OPTIMAL LOCATION FOR NEUROMODULATION FROM THE OVERALL UTILITY VALUE FOR EACH OF THE PLURALITY OF VOXELS

FIG. 7

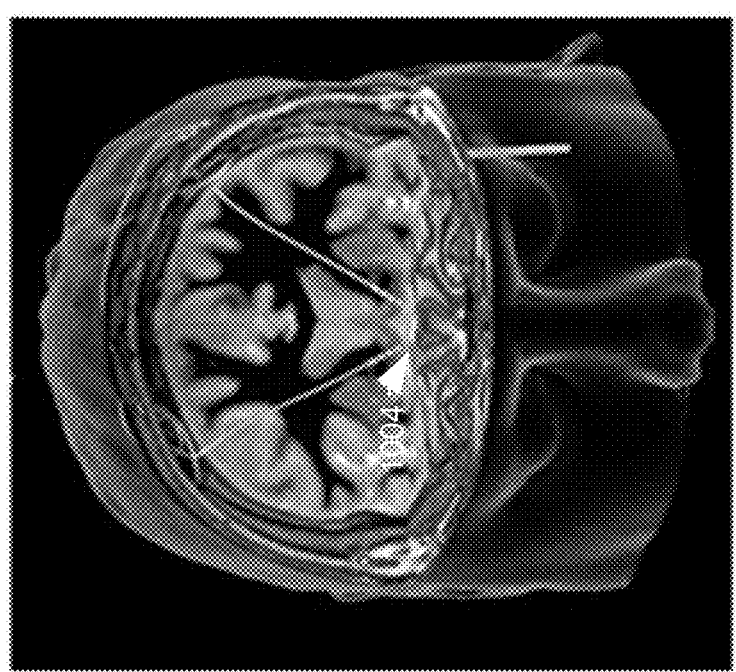
FIG. 12
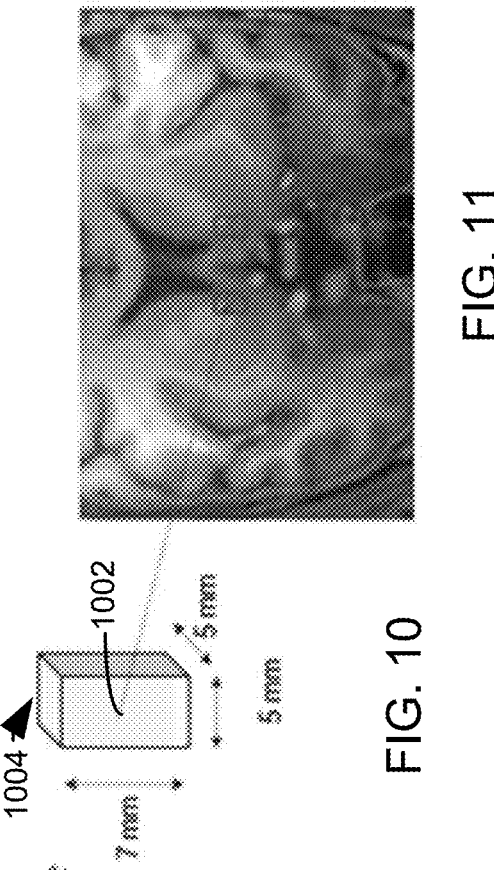
FIG. 11
FIG. 10

TARGETED NEUROMODULATION TO IMPROVE NEUROPSYCHIATRIC FUNCTION

RELATED APPLICATION

This application claims priority to U.S. Provisional Application No. 63,400,960, filed on Aug. 25, 2022 and entitled: "FOCUSED NEUROMODULATION TO IMPROVE NEUROPSYCHIATRIC FUNCTION," U.S. patent Ser. No. 18/310,465, filed May 1, 2023 and entitled "SCREENING, MONITORING, AND TREATMENT FRAMEWORK FOR FOCUSED ULTRASOUND," and U.S. patent Ser. No. 18/227,270, filed Jul. 27, 2023 and entitled "ANALYSIS FRAMEWORK FOR EVALUATING HUMAN WELL-NESS." Each of these applications is hereby incorporated by reference in their entirety.

TECHNICAL FIELD

This disclosure relates generally to the field of medical systems, and more particularly to targeting of neuromodulation treatment for neuropsychiatric functions.

BACKGROUND

Tractography is performed using data from diffusion MRI. The free water diffusion is termed "isotropic" diffusion. If the water diffuses in a medium with barriers, the diffusion will be uneven, which is termed anisotropic diffusion. In such a case, the relative mobility of the molecules from the origin has a shape different from a sphere. This shape is often modeled as an ellipsoid, and the technique is then called diffusion tensor imaging. Barriers can be many things: cell membranes, axons, myelin, etc.; but in white matter the principal barrier is the myelin sheath of axons. Bundles of axons provide a barrier to perpendicular diffusion and a path for parallel diffusion along the orientation of the fibers.

SUMMARY OF THE INVENTION

In accordance with one aspect of the invention, a method is provided for targeting neuromodulation in a brain of a patient for one of improving, diagnosing, and managing a neuropsychiatric function. A first image, representing a structure of the brain, is acquired from a first imaging system and a second image, representing a connectivity of the brain, is acquired from one of the first imaging system and a second imaging system. A first utility value associated with directly modulating tissue within a region of interest is determined for each of a plurality of voxels within the region of interest from the first image. A second utility value associated with indirectly modulating tissue outside of the region of interest by modulating tissue within the region of interest is determined for each of the plurality of voxels from the second image. An overall utility value for each of the plurality of voxels is determined from at least the first utility value and the second utility value. An optimal location for neuromodulation is determined from the overall utility value for each of the plurality of voxels.

In accordance with another aspect of the invention, a system is provided. An imagining interface receives a first image, representing a structure of the brain, from a first imaging system and a second image, representing a connectivity of the brain, from one of the first imaging system and a second imaging system. A targeting component determines a first utility value associated with directly modulating tissue within a region of interest for each of a plurality of voxels within the region of interest from the first image and determines a second utility value associated with indirectly modulating tissue outside of the region of interest by modulating tissue within the region of interest for each of the plurality of voxels from the second image. The targeting component then determines an overall utility value for each of the plurality of voxels from at least the first utility value and the second utility value and determines an optimal location for neuromodulation from the overall utility value for each of the plurality of voxels. A neuromodulation system delivers neuromodulation to the optimal location.

In accordance with a further aspect of the invention, a method is provided for improving neuropsychiatric function in a patient. A volume of influence having a center point within a target region comprising the nucleus accumbens and the ventral internal capsule that is between seven millimeters (mm) to twelve mm lateral from midline on the right and left sides of the brain, between one mm to six mm anterior to the anterior commissure (AC), and between two mm above to two mm below the AC is selected. Neuromodulation is delivered to the selected volume of influence.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 6 illustrates a method for determining a risk of a neuropsychiatric function from imaging of a brain of a patient; and FIG. 7 is a schematic block diagram illustrating an exemplary system of hardware components capable of implementing examples of the systems and methods disclosed in FIGS. 1-6.

FIG. 10 is a schematic illustration of an exemplary treatment site and a volume of influence of neuromodulation for addiction.

FIG. 11 is a coronal view of a brain MRI scan slice schematically illustrating the exemplary treatment site;

FIG. 12 is an illustration of an MRI image of a brain having implanted DBS electrodes; and FIG. 13 is a schematic block diagram illustrating an exemplary system of hardware components capable of implementing examples of the systems and methods disclosed in FIGS. 1-12.

DETAILED DESCRIPTION

Figure 1:
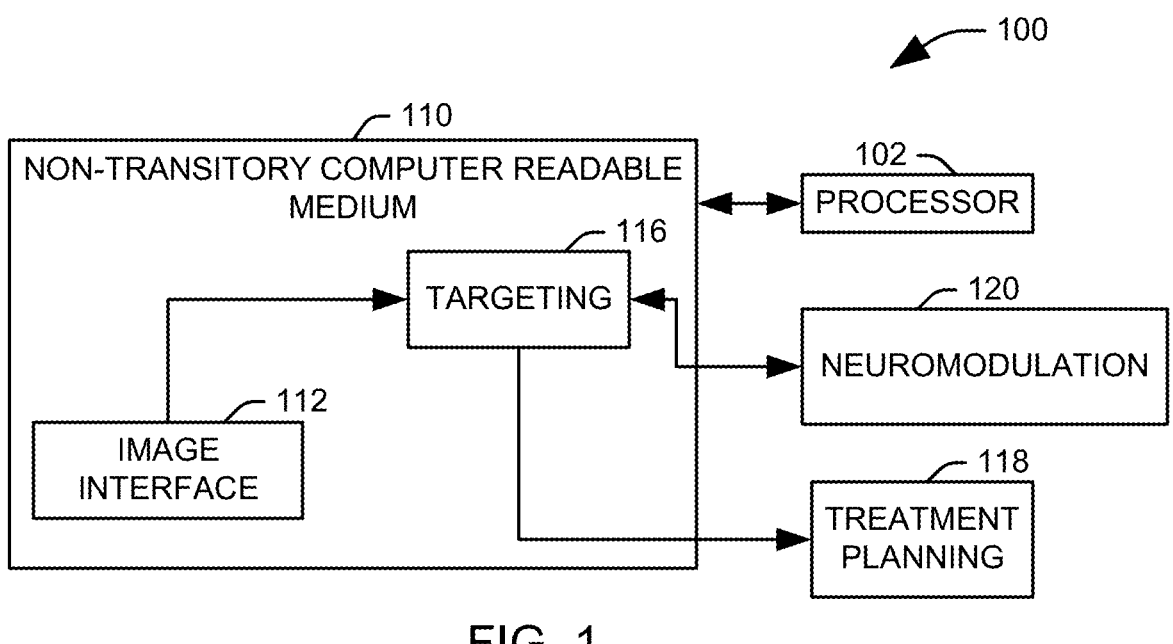
FIG. 1 illustrates a system for targeting neuromodulation for treatment or diagnosis of neuropsychiatric functions to a specific region of the brain of a patient.

Various examples of the systems and methods described herein utilize connectomes of the brain registered to anatomical imaging to determine an optimal location and shaping for applied neuromodulation. Neuromodulation techniques generally involve sending energy into specific brain areas to alter neuronal, axonal, and overall neural, nervous system, nerve activity, and targeting of neuromodulation has traditionally been based on anatomical structures. Unfortunately, this requires more coarse modulation settings and a timely titration period to achieve desired effects. The present disclosure relates to using information based on individual nervous system pathways to specifically locate areas that target precise brain areas with corresponding pathways being modulated to optimize desired effects. Further, the system can supplement this data with a comprehensive bioparameter-guided detection and prediction of functional status and symptom and disease status, network as well as biobehavioral, cognitive feedback, virtual reality cues, and imaging to quantify state of function, symptom and disease status and observation with screening and other treatments with neuromodulation. In one example, screening can be performed via a micro-treatment with focused ultrasound, and the patient can be evaluated to see if the treatment was effective. If not, a higher frequency and dose can be used. This screening can be performed for disease diagnosis, determining an appropriate therapy (e.g., medications, neuromodulation, other therapy), and determining a need, frequency, and dose for neuromodulation treatment.

A "neuromodulation technique or mode," or "neuromodulation" as described herein, is any suitable technique that applies localized energy (or other mode of neuromodulation) to the brain for the purpose of modulating (e.g., activating, inhibiting, regulating, resetting, normalizing) neural activity and neural networks or altering the permeability of the blood-brain barrier for an applied therapeutic at a specific location. Non-limiting neuromodulation techniques or modes include ultrasound such as, for example, focused ultrasound; electrical such as, for example superficial (including transcutaneous, percutaneous or subcutaneous stimulation) or cortical or deep brain stimulation, magnetic stimulation including, for example transcranial magnetic stimulation; optogenetic stimulation; or application of pulses of electromagnetic radiation. Other modes of neuromodulation include application of light, pressure, and heat/cold. As used herein, the term "modulation" refers to inhibiting, exciting, modulating, regulating, resetting or normalizing neural activity.

As used herein, a "predictive model" is a mathematical model or machine learning model that either predicts a future state of a parameter or estimates a current state of a parameter that cannot be directly measured.

As used herein, a "voxel" is an arbitrarily defined volume within a region in an image or model generated from an image representing a smallest unit of analysis within the image or model.

A "neuropsychiatric function," includes, for example, behavioral expression of brain function such as cognition, initiation, motivation, affect regulation, behavioral control, and perception and/or understanding of emotional stimuli characteristics (including processing speed). Other examples of neuropsychiatric function include general intellectual function, basic attention, complex attention (working memory), executive function, memory (visual and verbal), language, visio-constructional function, and visio-spatial construction. As such, non-limiting examples of neuropsychological functions include general intellectual function; attention, such as basic attention, the ability to monitor and direct attention, and the flexible allocation of attentional resources; working memory or divided attention which refers to a limited-capacity memory system in which information that is the immediate focus of attention can be temporarily held and manipulated (such as, for example, being able to simultaneously maintain two trains of thought in a flexible manner); executive functions which include, for example, planning, problem-solving skills, intentional and self-directed behavior, organizational skills, goal-directed behavior, the ability to generate multiple response alternatives, and maintenance of a conceptual set (i.e. the ability to maintain (or not lose) set or track of what one is doing); the ability to evaluate and modify behavior in response to feedback; verbal and visual memory, or the ability to retain and store new information for future use; visuo-spatial skills, such as judging how lines are oriented or discerning spatial relationships and patterns; visuo-constructional skills including two-dimensional construction skills (such as, for example, drawing or completing puzzles) and three-dimensional constructional skills (such as, for example, arranging blocks to match a design); language such as confrontation naming (such as, for example, naming specific words on demand, such as when shown a picture of the object), word fluency or generating a nonredundant list of words that belong to a specific category; motivation/drive/initiation in the interpersonal, cognitive or behavioral domains; affect regulation (such the ability to control and direct affect and mood in an context appropriate manner); and interpretation of emotion stimuli (such as the ability to interpret emotional facial expressions, posture, body language, prosody, and contextual information in order to infer another's emotional state or help identify an appropriate emotional response). A compromised neuropsychiatric function refers to an abnormality in the neuropsychiatric function compared to a normal, healthy population.

Compromised neuropsychiatric function can also include, for example, abnormal anxiety, stress, fear, mood, depression, obsessions, and compulsion. Compromised neuropsychiatric function can be improved in a wide variety of patients who exhibit compromised neuropsychiatric function, including patients suffering from a neuropsychiatric disorder, a psychiatric disorder, a neurodevelopmental disorder, or a neurodegenerative disorder. Non-limiting examples of such disorders include anxiety disorders, addiction, mood disorders, obsessive compulsive disorder (OCD), depression, post-traumatic stress disorder, bipolar disorder, autism, autism spectrum disorder, dyslexia, attention deficit disorder, acquired brain injury, stroke, schizophrenia and other forms of dementia, and Parkinson disease. With respect to addiction, the addiction includes addiction to an addictive behavior, an addictive chemical substance, or combinations thereof. Non-limiting examples of addiction to an addictive behavior include addiction to gambling, food (resulting in or correlated to, for example, obesity or an eating disorder), sex, shopping, sports and physical exercise, video gaming, media/internet use, pathological working, compulsive criminal behavior; and combinations thereof. Non-limiting examples of addiction to an addictive substance include addiction to nicotine; alcohol; cannabis; painkillers such as, for example, opioids; heroin; benzodiazepines; stimulants, such as, for example, amphetamines including methamphetamine and dextroamphetamine, and methylphenidate; inhalants such as, for example, gasoline, household cleaning products, and aerosols; sedatives/hypnotics such as, for example, barbiturates, zolpidem tartrate, and eszopiclone; and combinations thereof. Such conditions are merely examples of conditions where neuropsychological function can be compromised and thus is in need of improvement. Although the present disclosure is described primarily in the context of addiction, the methods and systems can be used for other conditions where the patient exhibits compromised neuropsychiatric function, such as, for example, Alzheimer's disease and related dementias and cognitive disorders that are inclusive but not limited to mild cognitive impairment (MCI), Lewy body dementia, frontotemporal dementia, vascular dementia, Parkinson's dementia, Chronic traumatic encephalopathy, Huntington's disease, Multi system atrophy, and others.

"Registration" of two or more images includes any process that assigns relative locations between pixels or multipixel features across two or more images. This assignation can be represented, for example, via an explicit transformation model between two or more images or via feature matching techniques that identify common structural features across two images.

An "intensity profile," as used herein, represents a spatial variation in the intensity of localized energy provided to the brain. An intensity profile can include a variance between two sides of a region provided with the localized energy or a more complex spatial variation of the energy.

FIG. 1 illustrates a system 100 for targeting neuromodulation for treatment or diagnosis of compromised neuropsychiatric functions to a specific region of the brain of a patient. The system 100 includes a processor 102 and a non-transitory computer readable medium 110 that stores executable instructions for targeting neuromodulation for treatment or diagnosis of compromised neuropsychiatric functions. The executable instructions include an imaging interface 112 that receives a first image, representing a structure of the brain, and a second image, representing a connectivity of the brain, for a patient from one or more associated imaging systems (not shown). In one implementation, the first image is a T1 magnetic resonance imaging (MRI) image, and the second image is a diffusion tensor imaging (DTI) image generated using an MRI imager. The imaging interface 112 can include appropriate software components for communicating with an imaging system (not shown) or repository of stored images (not shown) over a network via a network interface (not shown) or via a bus connection.

In some implementations, the imaging interface 112 can segment the first image into a plurality of subregions of the brain. The identified subregions can include, for example, a frontal pole, a temporal pole, a superior frontal region, a medial orbito-frontal region, a caudal anterior cingulate, a rostral anterior cingulate, an entorhinal region, a parahippocampal region, a peri-calcarine region, a lingual region, a cuneus region, an isthmus region, a pre-cuneus region, a paracentral lobule, and a fusiform region. For example, the first image is registered to a standard atlas to provide the segmentation. In another implementation, the imaging interface 112 can include a convolutional neural network, trained on a plurality of annotated image samples, can be used to provide the segmented image. One example of such a system can be found in 3D *Whole Brain Segmentation using Spatially Localized Atlas Network Tiles*, by Huo et al. (available at https://doi.org/10.48550/arxiv.1903.12152), which is hereby incorporated by reference in its entirety. The imaging interface 112 can also register the second image with the first image, such that the location of nodes within the connectome within the brain is known.

Each of the first image and the second image can be provided to a targeting component 116 that selects a location and intensity profile for the neuromodulation. The targeting component 116 generates a connectome of the brain, representing neural connections within the brain, from the second image. A region of interest can be defined within the first image, for example, based upon segmentation of the first image, and the location and intensity profile of the neuromodulation within the region of interest can be selected according to the generated connectome. It will be appreciated that the connectome can be determined as a passive connectome, representing the physical connectivity among portions of the brain, or an active connectome, representing the activity induced in portions of the brain in response to energy provided in a specific location.

The targeting component 116 can divide the defined region of interest into a plurality of voxels, and each voxel can be assigned a utility value based upon its location within the region of interest and its connection to other regions of the brain in the connectome to form a utility map. It will be appreciated that the term "utility value" is used broadly here to cover any method for assigning a value associated with neuromodulation to a region of tissue and is explicitly intended to cover both a cost approach in which positive values are assigned to regions for which application of energy is undesirable and a utility approach in which positive values are assigned to regions for which application of energy is desirable. In one example, the utility value for each voxel can be determined as a function of at least a first utility value, determined from the first image, and a second utility value, determined from the second image.

The first utility value can be determined, for example, from the type of tissue represented by each voxel. In one implementation, the region of interest from the first image can be registered to a standardized histology-based atlas for the region of interest containing values for various regions associated with the region of interest. In one example, the values in the histology-based atlas can be assigned according to an expected concentration of excitatory or inhibitory neurons across the population at each location, for example, as determined via analysis of histological samples representing the region of interest across a population of individuals. In one example, information from the second image can be used to adjust the values for the first utility value. For example, values in a hemisphere or region having low connectivity can be assigned a higher value, representing a potential to increase overall brain connectivity, or a lower value, representing a reduced secondary effect of the neuromodulation, depending on the specific disorder being treated. In the example of addiction, the region of interest can be all or a portion of the nucleus accumbens, and the ventral internal capsule and the neurons of interest can include, for example, GABAergic neurons, such as including medium spiny projection neurons (MNSs). For brain injuries and stroke, the values can be determined according to proximity or connectiveness to damaged brain tissue. For neurodevelopmental disorders, tissue within the nucleus accumbens having high concentration of excitatory or inhibitory neurons and networks can be assigned larger values to reduce anxiety and cravings. For epilepsy and pain, the region of interest can be located within the foci of the epilepsy, the surrounding cortical and sub-cortical brain tissue, afferent and efferent fibers to the damaged region as well as the thalamus, hippocampus, temporal lobe, insula, corpus callosum.

For stroke, the region of interest can be located, for example, within one or more of the area of the stroke, the surrounding cortical and sub-cortical brain tissue, afferent and efferent fibers to the damaged region as well as the thalamus, nucelus accumbens, motor cortex, sensory cortex, visual cortex, or language cortex. For stroke, the region of interest can be located, for example, within one or more of the area of brain injury, the surrounding cortical and sub-cortical brain tissue, afferent and efferent fibers to the damaged region as well as the thalamus, nucelus accumbens, motor cortex, sensory cortex, visual cortex, or language cortex. For Parkinson's disease, the region of interest can be located, for example, within one or more of the globus pallidum, subthalamic neuclus, thalamus, pulvinar of the thalamus, afferent and efferents to the thalamus. For neurodevelopmental disorders, the region of interest can be located, for example, within one or more of the thalamus and associated nuclei, sensory cortex, visual cortex, frontal lobe, afferent and efferents related to the sensory, visual and frontal lobe. For neurodevelopmental disorders, the region of interest can be located, for example, within one or more of the hippocampus, nucleus basalis of meynert, neucleus accumbens and internal capsuls, sensory cortex, parietal lobe, frontal lobe, calcarine cortex, temporal lobe. For each of these disorders, having high concentration of excitatory or inhibitory neurons and networks, depending o the specific disorder, can be assigned larger values. Similarly, where the patient exhibits any other compromised neuropsychiatric function, an appropriate region of interest can be located and treated as provided herein.

The second utility value can be determined from the second image, and represents the indirect modulation of neurons connected to a given voxel. Various regions of the brain, such as the frontal lobe, are often useful to modulate indirectly, whereas modulation of other regions, such as the amygdala, can lead to undesired side effects, such as anxiety. Using the connectivity data from the second image, a set of locations that are connected to each voxel can be determined, as well as a connection strength for each of the set of locations. The second utility value for each voxel can be determined as a weighted linear combination of the values for these locations, weighted by weights derived from the connection strengths for each location.

A volume of influence associated with neuromodulation has an associated intensity profile around a reference point, such as a center point, representing an amount of energy provided to the region for a given location of the reference point. In one example, each voxel can be assigned a value normalized by a maximum intensity, and this value can be used to weight the contribution of the voxel to the overall cost associated with the location and intensity profile. In other implementations, the intensity across the volume of influence can be assumed to be substantially uniform, such that no weighting is needed. Along with the utility value assigned to each of the voxels, each voxel can have one or more values representing the utility of applying a volume of influence centered on that voxel, for example, as the sum or weighted sum of all voxels within the volume of influence. It will be appreciated that the volume of influence can itself be changed, by adding additional focal points in focused ultrasound or selectively activating electrodes or changing the direction and intensity of the field produced by electrodes in deep brain stimulation to adjust the intensity profile or shape of the volume of influence. An optimization process, such as gradient decent, can be used to search the region of interest for an optimal or near-optimal center point location and shape of the volume of influence, and the resulting values can be provided to a treatment planning system 118 for use in generating a treatment plan for the patient. In one example, the treatment planning system 118 can be constrained to select a volume of influence having a center point that is between seven millimeters (mm) to twelve mm lateral from midline on the right and left sides of the brain, between one mm to six mm anterior to the anterior commissure (AC), and between two mm above to two mm below the AC In one example, the targeting component 116 can operate in conjunction with a neuromodulation system 120 to refine the map of the connectome of the brain. Specifically, energy can be applied at various locations within the region of interest, and activity within the brain can be determined via an appropriate functional imaging modality to determine if the change in brain activity expected from the second image is realized after application of the neuromodulation. Generally, these images can be acquired while the patient is performing a task or experiencing a cue that is relevant to their disorder. Additionally or alternatively, changes in connectivity in the brain after treatment can be used to as a measure of brain connectivity and used to refine parameters in the targeting component. In one implementation, activity measured within the brain in response to neuromodulation to a given location is recorded as a result of neuromodulation for that location. This can be used both to revise the weights applied to each of the set of connections for each voxel as well as the values applied to the voxels themselves for the patient. Further, the targeting component can be updated generally from this feedback to alter parameters associated with targeting for other patients, such as the values stored in the histology-based atlas for the region of interest or the assignment of connection strengths using the connectivity data in the second image, It will be appreciated that multiple locations can be impacted when energy is provided, and the detected activity can be attributed to each location, for example, represented as voxels, according to the percentage of energy received at each voxel. Alternatively, the results of multiple measurements can be compared, for example, via solving for one or more n-dimensional linear systems, where n is the number of voxels within the region of interest. Accordingly, the active connectivity associated with each location within the region of interest can be determined and used to adjust the values and connection weights associated with each of the plurality of voxels.

Figure 2:
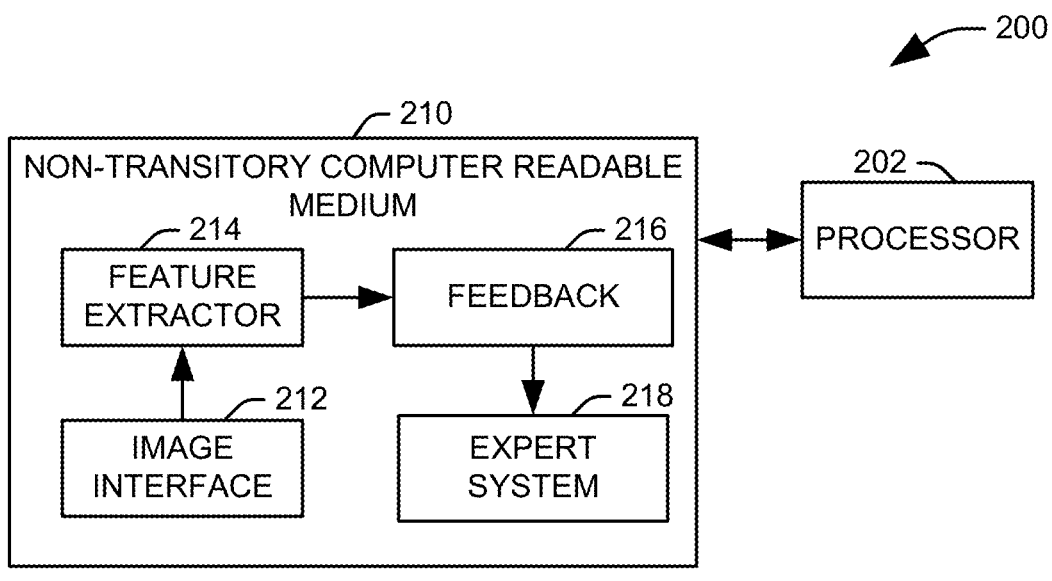
FIG. 2 illustrates a system for evaluating the effects of neuromodulation on one or more patients.

FIG. 2 illustrates a system 200 for evaluating the effects of neuromodulation on one or more patients. The system 200 includes a processor 202 and a non-transitory computer readable medium 210 that stores executable instructions for targeting neuromodulation for treatment and diagnosis of compromised neuropsychiatric functions. The executable instructions include an imaging interface 212 that receives a first image, representing a structure of the brain, and a second image, representing a connectivity of the brain, for a patient. In one implementation, the first image is a T1 magnetic resonance imaging (MRI) image, and the second image is a diffusion tensor imaging (DTI) image generated using an MRI imager. The imaging interface 212 can also receive functional images, for example, from a same or a different MRI imager, representing activity within the brain. The imaging interface 212 can include appropriate software components for communicating with an imaging system (not shown) or repository of stored images (not shown) over a network via a network interface (not shown) or via a bus connection.

The first image is provided to a registration component 214 that segments the first image into a plurality of subregions of the brain. The identified subregions can include, for example, a frontal pole, a temporal pole, a superior frontal region, a medial orbito-frontal region, a caudal anterior cingulate, a rostral anterior cingulate, an entorhinal region, a parahippocampal region, a peri-calcarine region, a lingual region, a cuneus region, an isthmus region, a pre-cuneus region, a paracentral lobule, and a fusiform region. In one example, the registration component 214 registers the first image to a standard atlas to provide the segmentation. In another implementation, a convolutional neural network, trained on a plurality of annotated image samples, can be used to provide the segmented image. The registration component 214 can also register the second image with the first image, such that the location of nodes within the connectome within the brain is known. In addition to the use of the first image for registration, various biometric parameters can be extracted from the image, including parameters related to connectivity, networks, grey/white mater ratio, and volume.

Each of the segmented first image and the second image can be provided to a feedback component 216 that determines the effectiveness of treatment for a patient according to patient data collected in response to stimuli. The stimuli can be applied neuromodulation in a given region or the presentation of cues associated with the patient's disorder being provided to the patient. One example of the presentation of cues can be found in U.S. Patent Publication No. US 2021/0162217, filed Dec. 2, 2020, and entitled "METHODS AND SYSTEMS OF IMPROVING AND MONITORING ADDICTION USING CUE REACTIVITY," which is hereby incorporated by reference in its entirety. During presentation of a given stimulus, electrical activity of the brain or other physiological activity can be recorded to determine whether neural activity increases, decreases or otherwise changes in response to the stimulus. The collected feedback can also include self-reporting from the patient, observations by clinicians, the measured electrical activity, measured biometric parameters, such as heart rate variability and blood pressure, and other relevant parameters.

In one implementation, the identified activity can be utilized as feedback for determining the success of a treatment of the patient via neuromodulation. This can be done during or immediately after treatment ("acute feedback"), a short time (e.g., hours to days) after a treatment ("semi-acute feedback") or a longer time (e.g., weeks to months after a treatment ("chronic feedback"). The cue can be selected to gauge the effect of the treatment on the disorder and can include addiction-related cues (e.g., pictures, aromas, flavors, or sounds associated with an addictive activity), activities measuring a capacity of the patient (e.g., memory and attention tasks), or other cues appropriate to evaluating the effects of a given disorder on the patient.

In certain aspects, a measurement of the patient's baseline craving level for the addictive behavior or the addictive chemical substance can be obtained. These baseline levels, which can be taken at various time points before or during therapy, can be taken while the patient is under a standard of care for addiction as outlined, for example, by the American Society of Addiction Medicine (ASAM 2013). These baseline levels can be taken at intake, during the course of medicated assisted, and/or behavioral treatment. Such baseline craving levels can be measured in a clinical/laboratory setting. Further, these baseline levels can shift or change over time during the course of treatment. Craving can be assessed, for example, by asking the patient to rate his or her craving to the substance or behavior for which the patient is seeking therapy via a 100-point visual analog scale (VAS) where 100 represents maximum craving and 0 represents no craving. After this baseline craving assessment, a method can comprise exposing the patient to a cue associated with the addictive behavior or addictive chemical substance followed by an assessment of the patient resultant craving level to determine changes in craving during or following cue exposure. The patient's resultant or subsequent craving level is measured proximate in time during or after exposure to the cue such that the patient's resultant craving level correlates to the patient's response to the cue. For example, the resultant craving level can be measured during exposure to the cue, within five minutes after exposure to the cue, within ten minutes after exposure to the cue, or any measurable time periods therebetween. More specifically, a method can comprise obtaining a measurement of the resultant patient's craving level for the addictive behavior or addictive chemical substance proximate in time during or after exposure to the cue and determining if there is an increase in the patient's resultant craving level or if the patient's resultant craving level remains substantially the same or decreases compared to the baseline craving level. A method can then comprise providing or adjusting neuromodulation based on a comparison of the baseline craving level and the resultant craving level to improve the patient's addiction. For example, neuromodulation can be provided or adjusted upon a determination that the resultant craving level increases above the patient's baseline craving level.

In certain aspects, a patient's craving level is not measured but rather a physiological, cognitive, psychosocial or behavioral parameter relevant to the patient's addictive behavior or addictive chemical substance of the patient is measured. In particular, a method can comprising obtaining a measurement of a baseline value of a physiological, cognitive, psychosocial, or behavioral parameter of the patient. As stated above, these baseline levels can change over time during the course of treatment. After this initial assessment, a method can comprise exposing the patient to a cue associated with the addictive behavior or the addictive chemical substance followed by an assessment of the patient's resultant parameter value to determine changes in the parameter value during or following cue exposure. The patient's resultant or subsequent parameter value is measured proximate in time during or after exposure to the cue such that the patient's resultant parameter measurement value correlates to the patient's response to the cue. More specifically, a method can comprise obtaining a measurement of a resultant value of the parameter proximate in time during or after exposure to the cue to determine if there is an increase in the resultant value of the parameter or if the resultant parameter value remains substantially the same or decreases compared to the baseline parameter value. The method can then comprise providing or adjusting neuromodulation to the patient based on a comparison of the resultant parameter value and the baseline parameter value. For example, neuromodulation can be provided or adjusted based upon a determination that the resultant parameter value increases above the patient's baseline parameter value.

The cue to which the patient is exposed can be a visual cue, a gustatory cue, an auditory cue, a tactile cue, an olfactory cue, or combinations thereof. The patient can be exposed to the cues via a smart phone, tablet, personal computer, or laptop, for example, in a naturalistic non-clinical setting such as when the patient is at home, work or other non-clinical setting. The patient can be exposed to the cues via virtual reality, augmented reality, or mixed reality. The patient can be exposed to multiple cues during any assessment period and, in the case of polysubstance use or behavior, the patient can be exposed to cue associated with the different addictive substances or behaviors. In the case of addiction to a chemical substance, the cue can be, for example, images of drugs, drug paraphernalia, or individuals using drugs. The cue can be specific for the particular addictive behavior or addictive chemical substance for which the patient is seeking therapy and can include multiple cues, including multiple different types of cues. For example, if the patient is addicted to alcohol, the cue can be the scent of alcohol, a visual image of a bar, or the sound of an alcoholic beverage container being opened. If the patient is addicted to heroin, the cues can be visual images of heroin, a hypodermic needle, or a spoon and lighter, for example. If the patient is addicted to gambling, the cue can be a visual image of a casino or gambling chips, for example. The above examples are only exemplary and are meant to point out that the cues can be addiction specific and can stimulate different senses. The cues can also be similar to the patient's characteristics such as, for example, the patient's age, gender, ethnicity, preferred chemical substances and routes of administration. In other words, the cues to which the patient is exposed can be personalized to the specific patient seeking therapy.

In aspects where a patient's physiological parameter is measured, the physiological parameter can be a response of the patient's autonomic nervous system to cue exposure and multiple physiological parameters can be measured during any given assessment session. The physiological parameters can be measured via a wearable device such as a ring, watch, or belt or via a smart phone or tablet, for example, in a naturalistic non-clinical setting such as when the patient is at home, work or other non-clinical setting. Exemplary physiological parameters include heart rate, heart rate variability, perspiration, salivation, blood pressure, pupil size, brain activity, electrodermal activity, body temperature, and blood oxygen saturation level. Table I provides non-limiting examples of physiological parameters that can be measured and exemplary tests to measure the physiological parameters.

TABLE I

| Physiological Parameter | Exemplary Devices and Methods to Measure Physiological Parameters |
| --- | --- |
| Brain Activity | Electroencephalogram, Magnetic Resonance Imaging, including functional Magnetic Resonance Imaging (IMRI), PET, SPECT, MEG, near-infrared spectroscopy, functional near-infrared spectroscopy, and other brain imaging modalities looking at electrical, blood flow, neurotransmitter, and metabolic MRI, taken either during a cognitive task or while the patient is at rest |
| Brain Structure | Magnetic Resonance Imaging |
| Heart rate | Electrocardiogram and Photoplethysmogram |
| Heart rate variability | Electrocardiogram, Photoplethysmogram |
| Eye tracking | Pupillometry, including tracking saccades, fixations, and pupil size (e.g., dilation) |
| Perspiration | Perspiration sensor |
| Retinal | OCT and angiography |
| Retinal anatomy, layers, retinal vasculature | Other Retinal imaging including wide field |
| Blood pressure | Sphygmomanometer |
| Body temperature | Thermometer, infrared thermography |

TABLE I-continued

| Physiological Parameter | Exemplary Devices and Methods to Measure Physiological Parameters |
| --- | --- |
| Blood oxygen saturation and respiratory rate | Pulse oximeter/accelerometer |
| Skin conductivity | Electrodermal activity |
| Facial emotions | Camera or EMG based sensors for emotion and wellness |
| Sympathetic and parasympathetic tone | Derived from the above measurements |

The physiological parameters can be measured in clinical settings with appropriate devices or in non-clinical settings via wearable, implantable, or portable devices. Some information can also be determined from self-reporting by the user via applications in a mobile device or via interaction with applications on the mobile device. For example, a smart watch, ring, or patch can be used to measure the user's heart rate, heart rate variability, body temperature, blood oxygen saturation, movement, and sleep. In a non-clinical setting, these values can also be subject to a diurnal analysis to estimate variability. Eye tracking can be performed, for example, using a camera on a mobile device and specialized software.

Table II provides non-limiting examples of cognitive parameters that are gamified and that can be measured and exemplary methods and tests/tasks to measure such cognitive parameters. The cognitive parameters can be assessed by a battery of cognitive tests that measure, for example, executive function, decision making, working memory, attention, and fatigue.

TABLE II

| Cognitive Parameter | Exemplary Tests and Methods to Measure Cognitive Parameters |
| --- | --- |
| Temporal discounting | Kirby Delay Discounting Task |
| Alertness and fatigue | Psychomotor Vigilance Task, go/no-go, reaction time, |
| Focused attention and response inhibition | Erikson Flanker Task |
| Working memory | N-Back Task, Change detection, spatial verbal and visual working memory tests |
| Attentional bias towards emotional cues | Dot-Probe Task |
| Inflexible persistence | Wisconsin Card Sorting Task |
| Decision making | Iowa Gambling Task |
| Risk taking behavior | Balloon Analogue Risk Task |
| Inhibitory control | Saccade and Anti-Saccade Task |
| Sustained attention | Sustained Attention |
| Executive function | Task Shifting or Set Shifting Task |
| Long term memory | Identifying pictures of famous people and other memory related tasks |
| Neuropsychological test | Montreal Cognitive Assessment (MoCA), Wide Range Achievement Test -reading subtest (WRAT-4), Judgement of Line Orientation (JOLO), Rey Osterrieth Complex Figure Test (ROCFT), Hooper Visual Organization Test (HVOT), Trail Making Test Versions A and B, Digit Span WAIS4, Phonemic Fluency FAS, Animal Naming test ANT, Mini-Mental State Examination (MMSE) |

These cognitive tests can be administered in a clinical/laboratory setting or in a naturalistic, non-clinical setting such as when the user is at home, work or other non-clinical setting. A smart device, such as a smartphone, tablet, or smart watch, can facilitate measuring these cognitive parameters in a naturalistic, non-clinical setting. For example, the Erikson Flanker, N-Back and Psychomotor Vigilance Tasks can be taken via an application on a smart phone, tablet, or smart watch. In one example, the patient can be allowed to explore a virtual reality environment and collect items within the environment. The patient is then asked to recount where each item was found within the virtual environment and the relationship of that location to a starting point, testing the patient's ability to recall spatial relationships among the virtual locations.

TABLE III provides non-limiting examples of parameters associated with movement and activity of the user, referred to herein alternatively for ease of reference as "motor parameters," that can be measured and exemplary tests, devices, and methods. The use of portable monitoring, physiological sensing, and portable computing devices allows the motor parameters to be measured. Using embedded accelerometer, GPS, and cameras, the user's movements can be captured and quantified to see how wellness affects them and related to the wellness-relevant parameters. Range of motion and gait analysis can be performed in a clinical setting using appropriate motion capture and camera equipment for evaluation.

TABLE III

| Motor/Musculoskeletal Parameter | Exemplary Tests and Methods to Measure Motor/Musculoskeletal Parameters |
|---|---|
| Activity level | Daily movement total, time of activities, from wearable accelerometer, steps, Motion Capture data, gait analysis, GPS, deviation from established geolocation patterns, force plates |
| Gait analysis | Gait mat, camera, force plates |
| Range of motion | Motion capture, camera, |
| Motor | Time up and go, 6-min walk test, perceptual motor tasks |

TABLE IV provides non-limiting examples of parameters associated with sensory acuity of the user, referred to herein alternatively for ease of reference as "sensory parameters," that can be measured and exemplary tests, devices, and methods.

TABLE IV

| Sensory Parameter | Exemplary Tests and Methods to Measure sensory Parameters |
|---|---|
| Vision | Visual acuity test, visual field tests, eye tracking, EMG |
| Hearing | Hearing tests |
| Touch | Two-point discrimination, frey filament |
| Smell/taste | |
| Vestibular | Vestibula function test |

TABLE V provides non-limiting examples of parameters associated with a sleep quantity, phases, and quality of the user, referred to herein alternatively for ease of reference as "sleep parameters," that can be measured and exemplary tests, devices, and methods.

TABLE V

| Sleep Parameter | Exemplary Tests and Methods to Measure Sleep Parameters |
|---|---|
| Sleep from wearables | Sleep onset & offset, sleep quality, sleep quantity, from wearable accelerometer, temperature, and PPG, |
| Sleep Questions | Pittsburg Sleep Quality Index, Functional Outcomes of Sleep Questionnaire, Fatigue Severity Scale, |

TABLE V-continued

| Sleep Parameter | Exemplary Tests and Methods to Measure Sleep Parameters |
|---|---|
| Devices | Epworth Sleepiness Scale Polysomnography; ultrasound, camera, bed sensors, EEG |
| Circadian Rhythm | Light sensors, actigraphy, serum levels, core body temperature |

TABLE VI provides non-limiting examples of parameters extracted by locating biomarkers associates with the user, referred to herein alternatively for ease of reference as "biomarker parameters," that can be measured and exemplary tests, devices, and methods. Biomarkers can also include imaging and physiological biomarkers related to a state of chronic wellness and improvement or worsening of the chronic wellness state.

TABLE VI

| Biomarkers Parameter | Exemplary Tests and Methods to Measure Biomarkers Parameters |
|---|---|
| Genetic biomarkers | Genetic testing |
| Immune biomarkers including TNF-alpha, immune alteration (e.g., ILs), oxidative stress, and hormones (e.g., cortisol) | Blood, saliva, and/or urine tests |

Table VII provides non-limiting examples of psychosocial and behavioral parameters, referred to herein alternatively for ease of reference as "psychosocial parameters," that can be measured and exemplary tests, devices, and methods.

TABLE VII

| Psychosocial or Behavioral Parameter | Exemplary Tests and Methods to Measure Psychosocial or Behavioral Parameters |
|---|---|
| Symptom log | Presence of specific symptoms (i.e., fever, headache, cough, loss of smell) |
| Medical Records | Medical history, prescriptions, setting for treatment devices such as spinal cord stimulator, imaging data |
| Wellness Rating | Visual Analog Scale, Defense & Veterans wellness rating scale, wellness scale, Wellness Assessment screening tool and outcomes registry |
| Burnout | Burnout inventory or similar |
| Physical, Mental, and Social Health | User-Reported Outcomes Measurement Information System (PROMIS), Quality of Life Questionnaire |
| Depression | Hamilton Depression Rating Scale |
| Anxiety | Hamilton Anxiety Rating Scale |
| Mania | Snaith-Hamilton Pleasure Scale |
| Mood/Catastrophizing scale | Profile of Mood States; Positive Affect Negative Affect Schedule |
| Affect | Positive Affect Negative Affect Schedule |
| Impulsivity | Barratt Impulsiveness Scale |
| Adverse Childhood Experiences | Childhood trauma |
| Daily Activities | Exposure, risk taking |
| Daily Workload and Stress | NASA Task Load Index, Perceived Stress Scale (PSS), Social Readjustment Rating Scale (SRRS) |
| Social Determents of Health | Social determents of health questionnaire |

In addition to one or more combinations of physiological, cognitive, psychosocial, and behavioral parameters, clinical data can also be part of the multi-dimensional feedback approach to evaluate the effectiveness of treatment. Such clinical data can include, for example, the user's clinical state, the user's medical history (including family history), employment information, and residential status. In particular, functional imaging can be used to evaluate the effect of the neuromodulation of brain activity. For example, a reduction of activity in a region in which inhibitory neurons are targeted or an increase of activity in a region in which excitatory neurons are targeted can indicate that the neuromodulation was successful. Similarly, connectivity information, for example, determined via tractography, can be used to indicate changes in brain connectivity over time due to treatment. In particular, the quality, quantity and density of connections revealed via tractography, as well as the change in these values over time, can be indicative of the effectiveness of the treatment. and be used to guide changes in treatment frequency and parameters, as well as selection of the patients for treatment. This is of particular interest in addiction, in which increased connectivity from the nucleus accumbus to the frontal lobe can be an indication that therapy was successful as well as neurodevelopmental disorders, in which increased brain connectivity overall can indicate a response to treatment. Further, increased connections are a sign of increased neuroplasticity, which is indicative of improvement for traumatic brain injury and stroke.

The type of change of the patient's physiological parameter measurement values or craving level during or after cue exposure can influence whether neuromodulation is provided or if existing neuromodulation should be adjusted. For example, in terms of providing neuromodulation, if there is an increase in the patient's physiological parameter measurement value or craving level during or after cue exposure compared to the baseline physiological parameter measurement value or baseline craving level, a method can involve initiating neuromodulation. Conversely, if the physiological parameter measurement value or craving level during or after cue exposure is substantially the same as the baseline physiological parameter measurement value or baseline craving level, neuromodulation may not be applied. In terms of adjusting therapy in the context of neuromodulation, methods can involve adjusting the parameters or dosing of the neuromodulation such as, for example, the duration, frequency, or intensity of the neuromodulation. If there is an increase in the patient's physiological parameter measurement value or craving level during or after cue exposure compared to the baseline physiological parameter measurement value or baseline craving level, a method can involve adjusting the neuromodulation so that the neuromodulation is more effective. For example, if the patient was previously having FUS delivered for five minutes during a therapy session, the patient can have the FUS subsequently delivered for twenty minutes during each session or if the patient was having FUS delivered every thirty days, the patient can have FUS subsequently delivered every two weeks. Conversely, if the physiological parameter measurement value or craving level after cue exposure is substantially the same as the baseline physiological parameter measurement value or baseline craving level, the neuromodulation parameters may not need adjustment and subsequent neuromodulation sessions can serve primarily as maintenance sessions or the intensity, frequency or duration of the neuromodulation can be decreased, for example. Alternatively, if the physiological parameter measurement value or craving level during or after cue exposure is substantially the same as the baseline physiological parameter measurement value or baseline craving level, then the patient can stop receiving any subsequent neuromodulation. The above scenarios are only exemplary and are provided to illustrate that the presence and type of change of the patient's physiological parameter measurement values and craving levels during and after cue exposure can influence whether therapy is provided or if existing therapy should be adjusted or terminated.

Further, the degree of the patient's physiological, cognitive, psychosocial, or behavioral parameter measurement value during or after cue exposure as well as the degree of the patient's craving level during or after cue exposure can influence the parameters of initial or subsequent neuromodulation. For example, if the specific patient seeking therapy has a craving level during or after cue exposure that is higher than the average craving level of the same patient population (patients with the same addiction), the therapy can be more aggressive initially or subsequently (e.g. in the context of neuromodulation, the duration, frequency, or intensity of the neuromodulation can be greater than that provided to patients of the same patient population). Similarly, if the specific patient seeking therapy has a physiological, cognitive, psychosocial, or behavioral parameter measurement value during or after cue exposure that is higher than the average parameter measurement value of the same patient population, the therapy can be more aggressive initially or subsequently. Conversely, if the specific patient's craving level or parameter measurement value during or after cue exposure is lower than the average craving level or parameter measurement value of the same patient population, the therapy can be less aggressive initially or subsequently. In other words, the severity or degree of the patient's resultant craving level or resultant physiological, cognitive, psychosocial, or behavioral parameter measurement value during or after cue exposure (as well as baseline values and levels) can correlate to the degree or aggressiveness of the neuromodulation. The above scenarios are only exemplary and are provided to illustrate that the degree of change of the patient's physiological parameter measurement values and craving levels during and after cue exposure can influence the parameters of initial and subsequent therapy.

In certain aspects, the feedback is not in response to a cue but rather a comparison of one or more combinations of a physiological, a cognitive, a psychosocial, and a behavioral parameter of the patient. For example, obtaining a measurement of baseline values of one or more combinations of a physiological, a cognitive, a psychosocial, and a behavioral parameter of the patient can be obtained. The patient can then be exposed to neuromodulation such as an initial focused ultrasound signal, an initial deep brain stimulation signal, or an initial transcranial magnetic stimulation signal to a neural target site of the patient. A subsequent measurement can be obtained of resultant values of the one or more combinations of the physiological, the cognitive, the psychosocial, and the behavioral parameter of the patient during or after application of the initial focused ultrasound signal, the initial deep brain stimulation signal, or the initial transcranial magnetic stimulation signal. The resultant values can be compared to the baseline values to determine if the patient's addiction has improved. The neuromodulation can be adjusted upon a determination that the patient's addiction has not improved As stated above, if it is determined that the neuromodulation was not successful, the neuromodulation can be provided to a different target location. It will be appreciated that this system can operate in conjunction with the system of FIG. 1 to guide the selection of a new target location for neuromodulation. In particular, a new target can be selected for the neuromodulation, for example, via the targeting component 114 described in FIG. 1.

Presentation of the stimulus can be repeated to accumulate functional imaging information associated with each of a plurality of stimuli, which can be accumulated and stored in memory. Where the stimulus is applied neuromodulation, the location of the applied neuromodulation can be recorded with the function imaging information. The accumulated imaging information and the connectome can also be provided to an expert system 218 that identifies regions and nodes of the brain which react in response to stimuli, as well as correlations among the activity of regions and nodes, referred to here as co-activating locations. The identified co-activating locations can be informed by the connectome, such that only regions and nodes that are connected within the connectome are identified as co-activating. It will be appreciated that functional imaging information can be accumulated across a single patient, a set of patients with a particular type of neuropsychiatric function, a set of patients with a general category of neuropsychiatric functions, a set of patients with no neuropsychiatric function, or across a set of both patients with neuropsychiatric functions and patients without neuropsychiatric functions. Depending on the patient or set of patients used and the stimuli utilized, the results can represent brain circuit patents unique to the patient, biomarkers for a general class of neuropsychiatric functions or a specific type of neuropsychiatric function, or biomarkers associated with a response to neuromodulation or other treatment. The determined patterns can be used, for example, to guide treatment of a specific patient or for identifying biomarkers of a neuropsychiatric function in novel patients.

In one example, information gathered across a set of patients with either a general category of neuropsychiatric functions or a specific disorder can be used to guide the selection of an initial location for applying neuromodulation. For example, if a particular location, defined relative to one or more landmark structures within the brain, has been consistently successful across a set of patients with the same or a similar disorder, that location can be a default location for an initial treatment via neuromodulation. Feedback representing the patient's response to treatment can be gathered as described above, and a new location can be selected for the patient where needed. The new location can be determined from the connectivity information and the information gathered for the set of patients. In one implementation, an analogical reasoning system can be used to locate past patients with similar characteristics to a current patient, and locations that were successful in the similar patients can be used. The characteristics used for matching patients with analogous patients can include demographical characteristics, medical histories, measured biometric parameters, such as blood pressure and heart rate variability, observations of the patient in response to cues, and measured electrical activity in the brain during and after neuromodulation.

In another example, measured feedback from a patient, such as measured electrical activity and biometric parameters, can be used to detect a presentation of cues to a patient in an automated fashion. In this implementation, neuromodulation and measurement of electrical activity and biometric parameters can be provided by one or both of an implanted device and a wearable device, and periodic measurements of electrical activity can be taken to evaluate the patient. These measurements can be provided to the expert system 218, which in this implementation can be trained on data representing the patient's response to presented cues, to determine if the patient has encountered a cue relevant to the neuropsychiatric function of the patient. If it is determined that the patient is reacting to a cue in the environment, the device providing neuromodulation can be activated to provide immediate treatment to the patient, allowing for automated presentation of neuromodulation in response to environmental cues.

Figure 3:
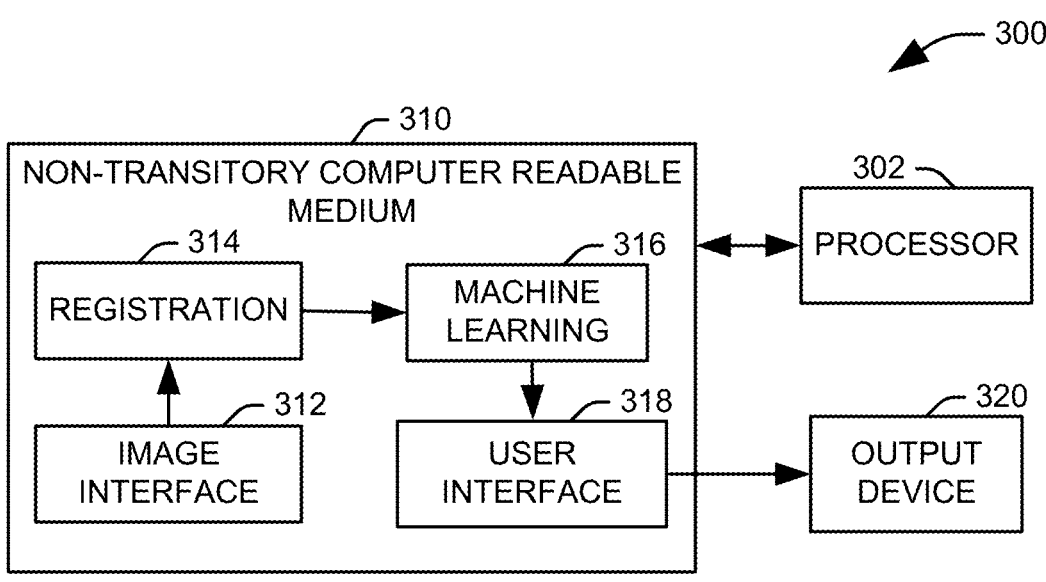
FIG. 3 illustrates a system for determining a risk or diagnosis verification of a neuropsychiatric function from imaging of a brain of a patient such as whom to select for treatment, how often to treat, facilitate the use of other treatment decisions for example.

FIG. 3 illustrates a system 300 for determining a risk of a compromised neuropsychiatric function from imaging of a brain of a patient. The system 300 includes a processor 302 and a non-transitory computer readable medium 310 that stores executable instructions for determining a risk of a neuropsychiatric function from imaging of a brain of a patient. The executable instructions include an imaging interface 312 that receives a first image, representing a structure of the brain, and a second image, representing a connectivity of the brain, for a patient. In one implementation, the first image is a T1 magnetic resonance imaging (MRI) image, and the second image is a diffusion tensor imaging (DTI) image generated using an MRI imager. The imaging interface 312 can also receive functional images, for example, from a same or a different MRI imager, representing activity within the brain. The imaging interface 312 can include appropriate software components for communicating with an imaging system (not shown) or repository of stored images (not shown) over a network via a network interface (not shown) or via a bus connection.

The first image is provided to a registration component 314 that segments the first image into a plurality of subregions of the brain. The identified subregions can include, for example, a frontal pole, a temporal pole, a superior frontal region, a medial orbito-frontal region, a caudal anterior cingulate, a rostral anterior cingulate, an entorhinal region, a parahippocampal region, a peri-calcarine region, a lingual region, a cuneus region, an isthmus region, a pre-cuneus region, a paracentral lobule, and a fusiform region. In one example, the registration component 314 registers the first image to a standard atlas to provide the segmentation. In another implementation, a convolutional neural network, trained on a plurality of annotated image samples, can be used to provide the segmented image. The registration component 314 registers the second image with the first image, such that the location of nodes within the connectome within the brain is known.

The registered second image is provided to a machine learning model 316. The machine learning model can utilize one or more pattern recognition algorithms, implemented, for example, as classification and regression models, each of which analyze a provided connectome image to assign a clinical parameter to the user representing one of a likelihood that a patient has or will have issues within a specified time period with a general class of neuropsychiatric functions, a likelihood that a patient has or will have issues within a specified time period with a specific neuropsychiatric function, a likelihood that a patient will respond to treatment for a neuropsychiatric function generally, or a likelihood that the patient will respond to a specific treatment for a neuropsychiatric function. It will be appreciated that the clinical parameter can be categorical or continuous. Where multiple classification and regression models are used, the machine learning model can include an arbitration element can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the patient.

The machine learning model, as well as any constituent models, can be trained on training data representing the various classes of interest. Training data can include, for example, the registered connectome image or numerical and/or categorical features extracted from the registered connectome image. For example, in supervised learning models, a set of examples having labels representing a desired output of the machine learning model can be used to train the system. The training process of the machine learning model will vary with its implementation, but training generally involves a statistical aggregation of training data into one or more parameters associated with the output classes. For rule-based models, such as decision trees, domain knowledge, for example, as provided by one or more human experts, can be used in place of or to supplement training data in selecting rules for classifying a user using the extracted features. Any of a variety of techniques can be utilized for the models, including support vector machines, regression models, self-organized maps, k-nearest neighbor classification or regression, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. In one implementation, the SVM can be implemented via a kernel method using a linear or non-linear kernel.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier. Another example is utilizing an autoencoder to detect outlier in wellness-relevant parameters as an anomaly detector to identify when various parameters are outside their normal range for an individual.

Many ANN classifiers are fully connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used. Regardless of the specific model employed, the clinical parameter generated at the machine learning model 316 can be provided to a user at the display 320 via a user interface or stored on the non-transitory computer readable medium 310, for example, in an electronic medical record associated with the patient.

In view of the foregoing structural and functional features described above, an example method will be better appreciated with reference to FIGS. 4-9. While, for purposes of simplicity of explanation, the example methods of FIGS. 4-9 are shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement a method in accordance with the invention.

Figure 4:
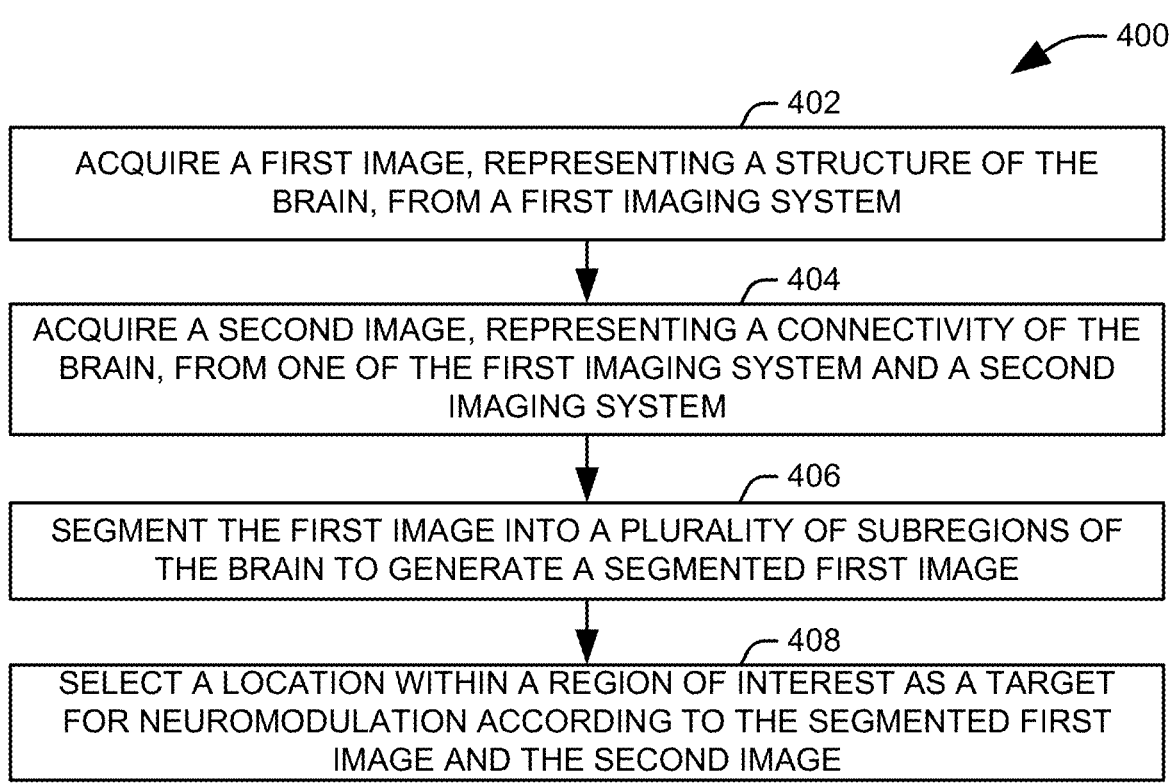
FIG. 4 illustrates a first method for targeting neuromodulation in a brain of a patient for treatment or diagnosis or management of a neuropsychiatric function.

FIG. 4 illustrates a first method 400 for targeting neuromodulation in a brain of a patient for treatment or diagnosis of a neuropsychiatric function. At 402 a first image, representing a structure of the brain, is acquired from a first imaging system. At 404, a second image, representing a connectivity of the brain, is acquired from one of the first imaging system and a second imaging system. In one implementation, the second image is one of a set of images representing the connectivity of the brain, each acquired by applying neuromodulation at a position within the region of interest associated with the image and measuring a level of activity in at least one of the plurality of subregions of the brain in response to applied neuromodulation. Additionally or alternatively, the second image can be acquired via diffusion tensor imaging.

At 406, the first image is segmented into a plurality of subregions of the brain to generate a segmented first image, such that each of at least a subset of a plurality of voxels comprising the first image are associated with one of the plurality of subregions. It will be appreciated that not all portions of the first image may be of interest for a given neuropsychiatric function, and thus only those voxels representing the plurality of subregions may be included in the segmentation. At 408, a location within a region of interest of the brain is selected as a target for neuromodulation according to the segmented first image and the second image.

Figure 5:
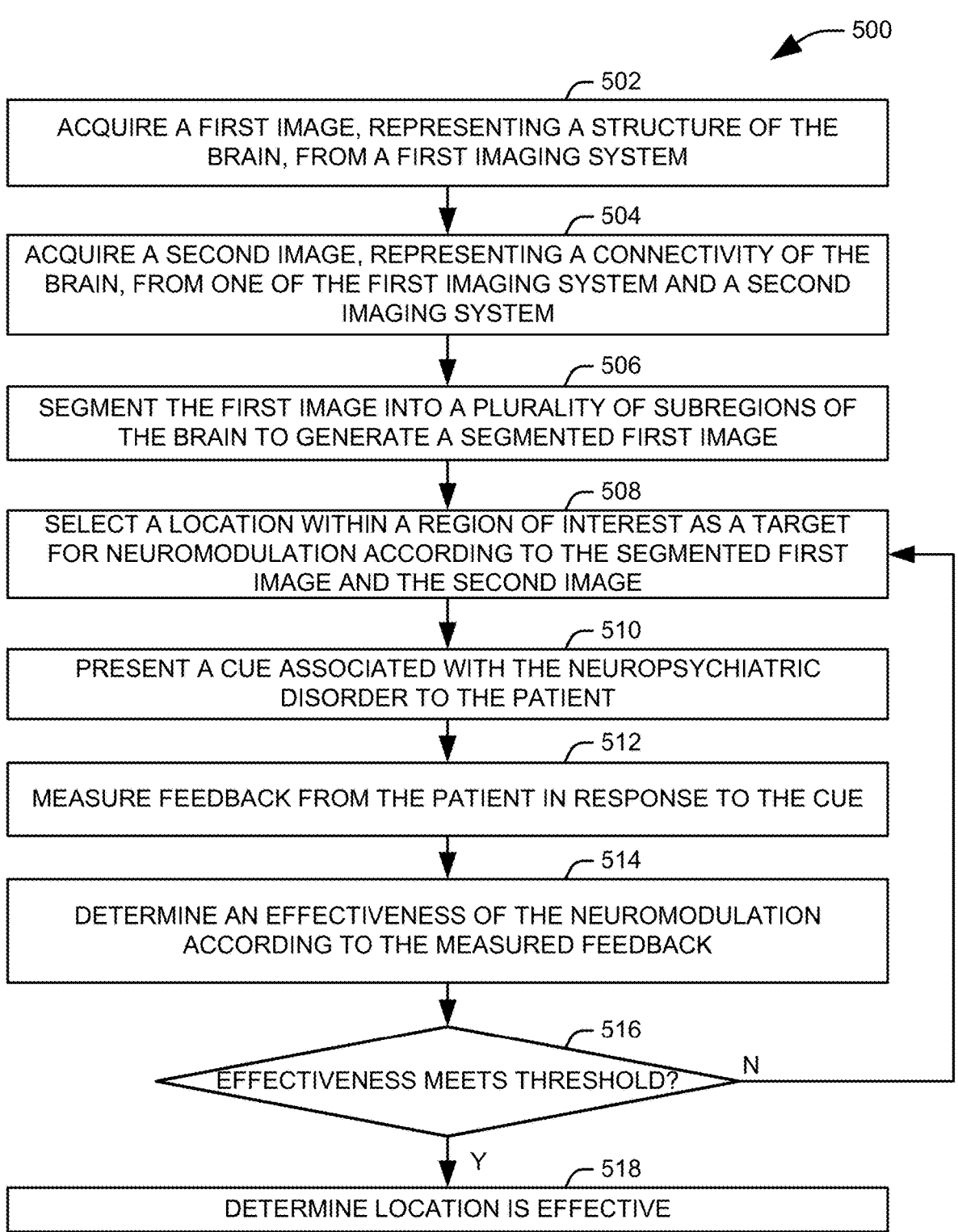
FIG. 5 illustrates a second method for targeting neuromodulation in a brain of a patient for treatment or diagnosis or management of a neuropsychiatric function.

FIG. 5 illustrates a second method 500 for targeting neuromodulation in a brain of a patient for treatment or diagnosis of compromised neuropsychiatric function. At 502 a first image, representing a structure of the brain, is acquired from a first imaging system. At 504, a second image, representing a connectivity of the brain, is acquired from one of the first imaging system and a second imaging system. In one implementation, the second image is one of a set of images representing the connectivity of the brain, each acquired by applying neuromodulation at a position within the region of interest associated with the image and measuring a level of activity in at least one of the plurality of subregions of the brain in response to applied neuromodulation. Additionally or alternatively, the second image can be acquired via diffusion tensor imaging.

At 506, the first image is segmented into a plurality of subregions of the brain to generate a segmented first image, such that each of at least a subset of a plurality of voxels comprising the first image are associated with one of the plurality of subregions. It will be appreciated that not all portions of the first image may be of interest for a given neuropsychiatric function, and thus only those voxels representing the plurality of subregions may be included in the segmentation. At 508, a location within a region of interest of the brain is selected as a target for neuromodulation according to the segmented first image and the second image.

At 510, a cue associated with the neuropsychiatric function is presented to the patient, and feedback from the patient in response to the cue is measured at 512. The feedback can include observations of a clinician on the appearance and behavior of the patient, self-reporting from the patient about symptoms of the disorder, measured electrical activity in the brain, and biometric parameters. At 514, an effectiveness of the neuromodulation is determined according to the measured feedback. At 516, it is determined if the effectiveness of the neuromodulation meets a threshold value. If so (Y), the location of the neuromodulation is determined to be effective at 518 and the method terminates. If not (N), the selected location is determined to be ineffective, and the method returns to 508 to select a new location within the region of interest as a target for neuromodulation. It will be appreciated that steps 510, 512, 514, and 516 can be performed during or immediately after treatment, a short time (e.g., hours to days) after a treatment, or a longer time (e.g., weeks to months after a treatment.

FIG. 6 illustrates a method 600 for determining a risk of a compromised neuropsychiatric function from imaging of a brain of a patient. At 602 a first image, representing a structure of the brain, is acquired from a first imaging system. At 604, a second image, representing a connectivity of the brain, is acquired from one of the first imaging system and a second imaging system. In one implementation, the second image is one of a set of images representing the connectivity of the brain, each acquired by applying neuromodulation at a position within the region of interest associated with the image and measuring a level of activity in at least one of the plurality of subregions of the brain in response to applied neuromodulation. Additionally or alternatively, the second image can be acquired via diffusion tensor imaging.

At 606, the first image is segmented into a plurality of subregions of the brain to generate a segmented first image, such that each of at least a subset of a plurality of voxels comprising the first image are associated with one of the plurality of subregions. It will be appreciated that not all portions of the first image may be of interest for a given comprised neuropsychiatric function, and thus only those voxels representing the plurality of subregions may be included in the segmentation. At 608, representation of the segmented first image and the second image to a machine learning model trained on imaging data for a plurality of patients having known outcomes, and at 610, a clinical parameter representing the risk of the patient for the compromised neuropsychiatric function is generated from the representation of the segmented first image and the second image.

In one implementation, a set of numerical features are extracted from the segmented first image and the second image, and the set of numerical features are provided to the machine learning model. In another implementation, the segmented first image and the second image are provided directly to the machine learning model. In still another implementation, the second image is registered with the first image to provide a registered connectome, representing the location of nodes within the connectome relative to the plurality of subregions, and either the registered connectome or a set of numerical features representing the registered connectome can be provided to the machine learning model. It will be appreciated that the clinical parameter can be any continuous or categorical parameter that represents a risk to the patient associated with the compromised neuropsychiatric function, including a likelihood that a patient will exhibit one of the compromised neuropsychiatric function and one of a plurality of compromised neuropsychiatric functions within a class of compromised neuropsychiatric functions that includes the compromised neuropsychiatric function, a likelihood that a patient has one of the compromised neuropsychiatric function and one of a plurality of compromised neuropsychiatric functions within a class of compromised neuropsychiatric functions that includes the compromised neuropsychiatric function, and a likelihood that a patient will respond to treatment for the compromised neuropsychiatric function. The clinical parameter can then be stored in a non-transitory computer readable medium or displayed to a user at an associated output device.

FIG. 7 illustrates a method 700 for targeting neuromodulation in a brain of a patient for one of improving, diagnosing, treating, and managing a neuropsychiatric function. At 702, a first image, representing a structure of the brain, is acquired from a first imaging system. For example, the first imaging system can be a computed tomography (CT) system or a magnetic resonance imaging (MRI) system. At 704, a second image, representing a connectivity of the brain, is acquired from one of the first imaging system and a second imaging system. For example, the second imaging system can be an MRI system, and the image can be generated via diffusion tensor imaging.

At 706, a first utility value associated with directly modulating tissue within a region of interest is determined for each of a plurality of voxels within the region of interest from the first image. In one example, this is done by identifying various tissue types in the first image and assigning values according to the tissue types. In another example, a portion of the first image representing the region of interest is registered to an histology-based atlas having assigned values for the first utility value for each of a plurality of locations within the histology-based atlas. These values can be determined, for example, according to a concentration of inhibitory neurons or excitatory neurons expected to be in a given location based on data, sch as histology data, captured across a population of interest.

At 708, a second utility value associated with indirectly modulating tissue outside of the region of interest by modulating tissue within the region of interest is determined for each of the plurality of voxels from the second image. In one example, for each voxel of the plurality of voxels, a set of locations outside of the region of interest that are indirectly modulated when the given voxel is modulated is determined from the second image. Each of the set of locations having an associated indirect utility value, representing the value of modulating that tissue generally. Respective strengths of a connection between the voxel and each of the set of locations can also be determined from the second image, with the strength between each of the set of locations and the given voxel being represented as a connection weight. It will be appreciated that the weight can be determined as a linear or non-linear function of the connection strength. The second utility value for each voxel can be as a sum of the products of the indirect utility values for its set of locations and the associated connection weight.

At 710, an overall utility value for each of the plurality of voxels is determined from at least the first utility value and the second utility value for that voxel. Each overall utility value can be determined as a linear or non-linear function of the first utility value and the second utility value. In one example, the overall utility value is a sum of the first utility value and the second utility value. At 712, an optimal location for neuromodulation from the overall utility value for each of the plurality of voxels. For example, an appropriate optimization algorithm, such as gradient decent or simulated annealing, can be used to find the optimal location. It will be appreciated that the neuromodulation will have a volume of influence with a center point and a shape, and that both an optimal location and an optimal shape for the volume of influence can be determined. In one example, in which the region of interest comprises at least a portion of the nucleus accumbens and the ventral internal capsule, the optimization can be constrained such that the volume of influence has a center point that is between seven millimeters (mm) to twelve mm lateral from midline on the right and left sides of the brain, between one mm to six mm anterior to the anterior commissure (AC), and between two mm above to two mm below the AC.

In one implementation, functional imaging, such as functional MRI or positron emission tomography (PET) can be used to evaluate the effectiveness of the neuromodulation and adjust the targeting accordingly, both for the current patient and future patients. For example, a third image, representing activity of the brain, can be acquired from an appropriate functional imaging system at a first time; and neuromodulation can be applied at the determined optimal location at a later second time A fourth image, representing activity of the brain, from the functional imaging system at lation. From this comparison, values such as the first utility value of voxels within the volume of influence and connection weights associated with voxels within the volume of influence can be adjusted based on the changes in brain activity attributed to the neuromodulation. Further, parameters associated with the targeting, such as the function used to calculate connection weights from connection strengths determined via tractography and histology-based atlas values used for the first utility value can be adjusted for future patients.

Figure 8:
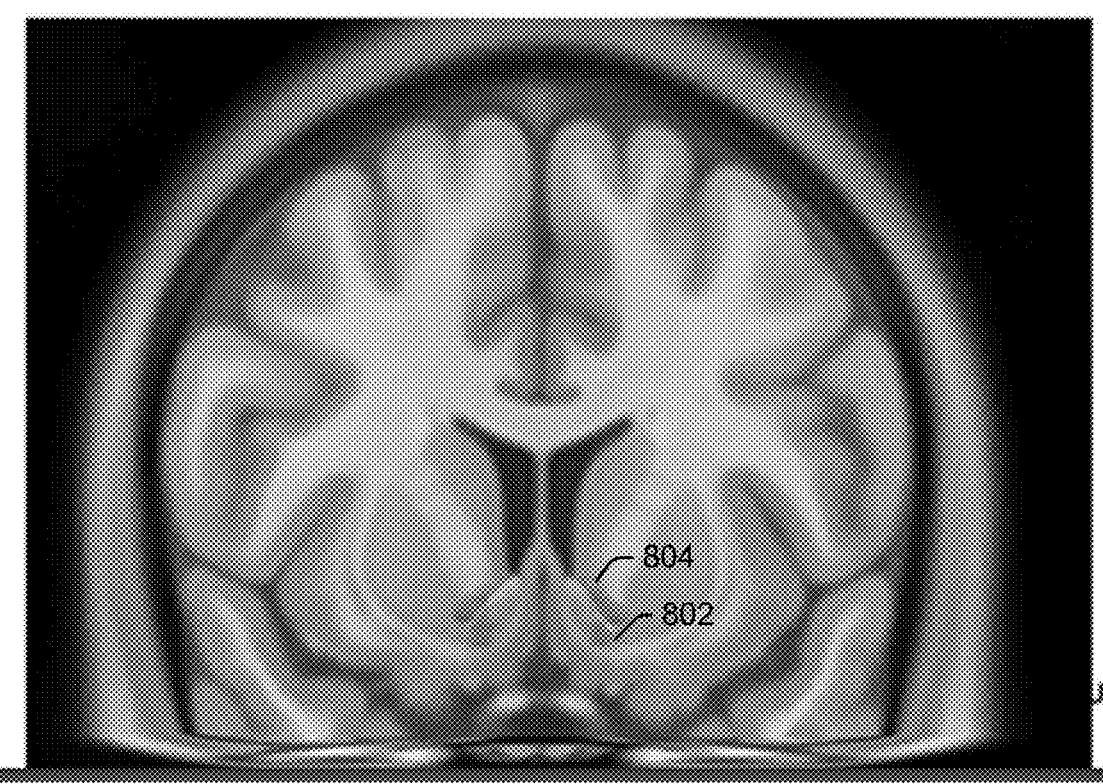
FIG. 8 is a coronal view of a brain MRI scan slice identifying the nucleus accumbens and internal capsule.
Figure 9:
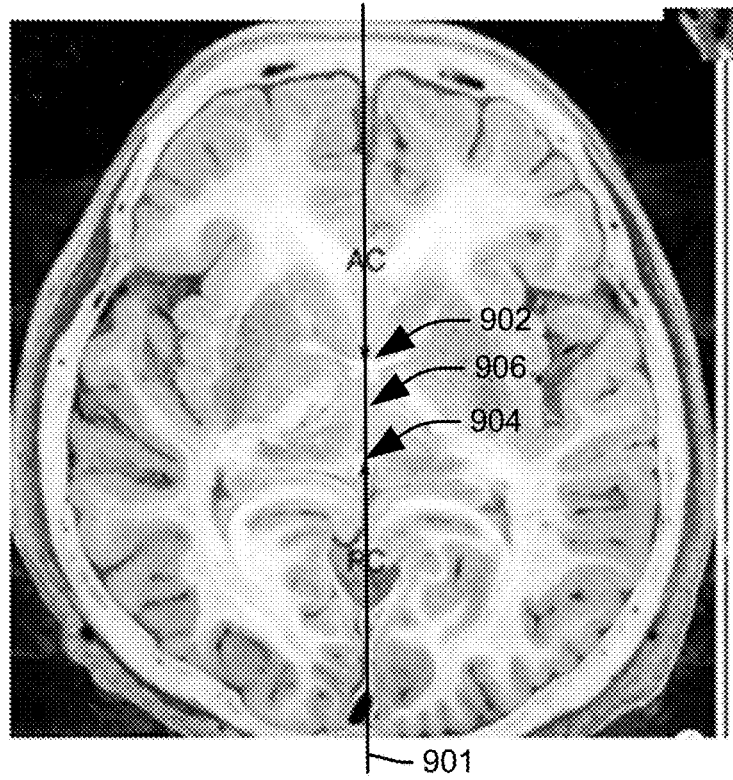
FIG. 9 is an axial view of a brain MRI scan slice identifying the anterior commissure, the posterior commissure, the midcommissural point and the midline of the brain.

In certain aspects and with reference to FIGS. 8 and 9, a method of improving addiction to an addictive behavior or addictive chemical substance in a patient is provided. Such a method can include delivering a FUS signal or a DBS signal to a treatment site comprising the nucleus accumbens 802, the ventral internal capsule 804, or both that is seven millimeters (mm) to twelve mm lateral from the midline 901 on the right and left sides of the brain, one mm to six mm anterior to the anterior commissure (AC) 902, and two mm superior to the AC to two mm inferior to the AC. The midline is an imaginary line that extends through the center of the brain. The AC 902 and the posterior commissure (PC) 904 are transversely oriented commissural white matter tract that connects the two cerebral hemispheres along the midline. The midcommissural point (MCP) 906 is the midpoint between the AC and the PC. The AC, PC, and the MCP are reference points or landmarks used in imaging methods such as MRI, PET, and CT. Although the above-referenced method is described with respect to the AC, the treatment site could be determined with respect to the PC or the MCP. Referring to FIGS. 10-12, in the case of FUS, the treatment site 1002 is the center of the volume of influence 1004 that directly receives the FUS signal. FIG. 10 illustrates a 5 mm×5 mm×7 mm volume of influence, but the volume of influence could differ with the region of the brain being treated (e.g. nucleus accumbens). In the case of DBS, illustrated in FIG. 12, the treatment site 1202 is the region of the brain where the center of the plurality of electrical contacts of the electrical lead is inserted into and that directly receives the electrical signal.

With respect to addiction, the neural target site to which stimulus is delivered can be a component of the patient's reward circuitry, such as, the nucleus accumbens and the ventral internal capsule. The stimulus can be applied to a neural target site unilaterally or bilaterally. Table VIII provides an exemplary list of neural target sites, exemplary forms of neuromodulation, and exemplary neuromodulation parameters that can be applied to these neural target sites as part of the patient's therapy.

TABLE VIII

| Exemplary Target Site | Exemplary Form of Neuromodulation | Exemplary Neuromodulation Parameters |
|---|---|---|
| Nucleus Accumbens and Ventral Internal Capsule | DBS and FUS | DBS parameters: frequency of ~1 Hz to ~10,000 Hz; pulse width of ~5 microseconds to ~1000 microseconds; intensity of ~0.1 v or mA to ~30 v or mA FUS parameters: sonication dose; power (~0 W-~150 W); sonication duration (~0 min-~30 min to ~60 min); frequency direction, repetition time on/off (5 sec; 10 sec), pulse duration on/off 10-1000 msec; 10-990 msec), continuous or burst; energy/minute (~0 J/min-~290 J/min; frequency (~.1-~3 MHz); and number of elements (~1-~1024) | a still later third time, and the third and fourth images can be compared to determine an effectiveness of the neuromodu- In certain aspects with respect to FUS, the dose includes a system frequency of 0.1 to 3 Mhz; an intensity or power of 10 W to 200 W; a pulse duration on/off of 10 msec to 1000 msec (on) and 10-990 msec (off); an overall duration of 30 seconds to 30 minutes; a number of ultrasound transducers/elements of between 1 and 1024. It will be appreciated that various ultrasound systems will have different operating parameters. Table IX has parameters associated with ultrasound systems that can be used with the systems and methods herein.

TABLE IX

|  | Insightec | Navifus | Brainsonix | Cordence Medical |
|---|---|---|---|---|
| Focal Width | 3 mm per sub spot | 3 mm per sub spot | 3.8 mm* 4.0 mm 4.4 mm | |
| Focal Length | 7 mm | 15 mm | 25 mm* 30 mm 42 mm | |
| Focal Depth | Steerable | Steerable 40~140 mm | 54 mm* 63.5 mm 78 mm | |
| Drive Frequency | ~230 kHz | (not found) | 250 kHZ~1.25 MHz (current transducer operates only at 650 kHz) | 220 KHz |
| Pulse Repetition Freq | Burst on: 100 ms Burst period: 3 s (current mode used) | Burst on: 2 µs~10 ms Burst period: 4 µs~1 s | 10~1000 Hz | |
| Duty Cycle | 3.33% | 0.0002%~50% | 5%~50% | |
| Guidance | MRI | Neuronavigation | MRI | |
| Elements | 1024 | 256~1024 | Single | |
| Max Power | >100 W | (not found) | 15 W average power (power * duty cycle) | |

*Values for three types of transducers

FIG. 13 is a schematic block diagram illustrating an exemplary system 1300 of hardware components capable of implementing examples of the systems and methods disclosed in FIGS. 1-12, such as the system for targeting neuromodulation illustrated in FIG. 1. The system 1300 can include various systems and subsystems. The system 1300 can be any of personal computer, a laptop computer, a workstation, a computer system, an appliance, an application-specific integrated circuit (ASIC), a server, a server blade center, or a server farm.

The system 1300 can includes a system bus 1302, a processing unit 1304, a system memory 1306, memory devices 1308 and 1310, a communication interface 1312 (e.g., a network interface), a communication link 1314, a display 1316 (e.g., a video screen), and an input device 1318 (e.g., a keyboard and/or a mouse). The system bus 1302 can be in communication with the processing unit 1304 and the system memory 1306. The additional memory devices 1308 and 1310, such as a hard disk drive, server, stand-alone database, or other non-volatile memory, can also be in communication with the system bus 1302. The system bus 1302 interconnects the processing unit 1304, the memory devices 1306-1310, the communication interface 1312, the display 1316, and the input device 1318. In some examples, the system bus 1302 also interconnects an additional port (not shown), such as a universal serial bus (USB) port.

The system 1300 could be implemented in a computing cloud. In such a situation, features of the system 1300, such as the processing unit 1304, the communication interface 1312, and the memory devices 1308 and 1310 could be representative of a single instance of hardware or multiple instances of hardware with applications executing across the multiple of instances (i.e., distributed) of hardware (e.g., computers, routers, memory, processors, or a combination thereof). Alternatively, the system 1300 could be implemented on a single dedicated server.

The processing unit 1304 can be a computing device and can include an application-specific integrated circuit (ASIC). The processing unit 1304 executes a set of instructions to implement the operations of examples disclosed herein. The processing unit can include a processing core.

The additional memory devices 1306, 1308, and 1310 can store data, programs, instructions, database queries in text or compiled form, and any other information that can be needed to operate a computer. The memories 1306, 1308 and 1310 can be implemented as computer-readable media (integrated or removable) such as a memory card, disk drive, compact disk (CD), or server accessible over a network. In certain examples, the memories 1306, 1308 and 1310 can comprise text, images, video, and/or audio, portions of which can be available in formats comprehensible to human beings.

Additionally or alternatively, the system 1300 can access an external data source or query source through the communication interface 1312, which can communicate with the system bus 1302 and the communication link 1314.

In operation, the system 1300 can be used to implement one or more parts of a system in accordance with the present invention. Computer executable logic for implementing the quality assurance system resides on one or more of the system memory 1306, and the memory devices 1308, 1310 in accordance with certain examples. The processing unit 1304 executes one or more computer executable instructions originating from the system memory 1306 and the memory devices 1308 and 1310. It will be appreciated that a computer readable medium can include multiple computer readable media each operatively connected to the processing unit.

In certain aspects, a method of improving compromised neuropsychiatric function in a patient is provided. Such a method comprises acquiring a parameter representing a connectivity of a brain of the patient, such as measuring stress, anxiety, or cravings for example. The parameter can be acquired by acquiring an image, representing the connectivity of the brain of the patient, via an imaging system and extracting the parameter representing the connectivity of a brain of the patient from the image. A physiological, cognitive, psychosocial, behavioral parameter, or combinations thereof relevant to the patient's compromised neuropsychiatric function is also measured. Therapy can be provided or adjusted based on the parameter representing the connectivity of the brain of the patient and the measurement of the physiological, cognitive, psychosocial, behavioral parameter or combinations thereof of the patient. The measurement of the physiological, cognitive, psychosocial, behavioral parameter, or combinations thereof can be in response to presentation of a cue related to a neuropsychiatric disorder manifesting the compromised neuropsychiatric function.

In certain aspects, a method is provided to screen an individual suffering from compromised neuropsychiatric function to determine if the individual is a suitable candidate for therapy. Such a method includes acquiring a parameter representing a connectivity of a brain of the patient. The parameter can be acquired by acquiring an image, representing the connectivity of the brain of the patient, via an imaging system and extracting the parameter representing the connectivity of a brain of the patient from the image. The method can also include measuring a physiological, cognitive, psychosocial, behavioral parameter, or combinations thereof relevant to the patient's compromised neuropsychiatric function; and determining if the individual is a suitable candidate for therapy based on the parameter representing the connectivity of the brain of the patient and the measurement of the physiological, cognitive, psychosocial, behavioral parameter, or combinations thereof of the patient. The measurement of the physiological, cognitive, psychosocial, behavioral parameter or combinations thereof can be in response to presentation of a cue related to a neuropsychiatric disorder manifesting the compromised neuropsychiatric function. Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments. 13

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof. Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function. Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, and volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine-readable mediums for storing information. The terms "computer readable medium" and "machine readable medium" includes, but is not limited to, portable or fixed storage devices, optical storage devices, wireless channels, and/or various other storage mediums capable of storing that contain or carry instruction(s) and/or data. It will be appreciated that a "computer readable medium" or "machine readable medium" can include multiple media each operatively connected to a processing unit.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

In view of the foregoing, the following is claimed:

1. A method for targeting neuromodulation in a brain of a patient for one of improving, diagnosing, and managing a neuropsychiatric function, the method comprising:

acquiring a first image, representing a structure of the brain, from a first imaging system;

acquiring a second image, representing a connectivity of the brain, from one of the first imaging system and a second imaging system;

determining a first utility value associated with directly modulating tissue within a region of interest for each of a plurality of voxels within the region of interest from the first image;

determining a second utility value associated with indirectly modulating tissue outside of the region of interest by modulating tissue within the region of interest for each of the plurality of voxels from the second image, wherein determining the second utility value for each of the plurality of voxels comprises:

determining, for a given voxel of the plurality of voxels, a set of locations outside of the region of interest that are indirectly modulated when the given voxel is modulated from the second image, each of the set of locations having an associated indirect utility value;

determining respective strengths of a connection between the given voxel and each of the set of locations from the second image, the strength between each of the set of locations and the given voxel being represented as a connection weight; and determining the second utility value for the given voxel as a sum of the products of the indirect utility value and connection weight for each of the set of locations;

determining an overall utility value for each of the plurality of voxels from at least the first utility value and the second utility value, each of first utility value, the second utility value, and the overall utility value representing a degree to which application of energy to the tissue represented by the voxel is desirable as one of a cost approach, in which positive values are assigned to regions for which application of energy is undesired and a utility approach in which positive values are assigned to regions for which application of energy is desirable; and determining an optimal location for neuromodulation from the overall utility value for each of the plurality of voxels; and applying neuromodulation at the optimal location.

2. The method of claim 1, further comprising:

acquiring a third image, representing activity of the brain, from one of the first imaging system, the second imaging system, and a third imaging system at a first time; after applying the neuromodulation at the optimal location, the neuromodulation having a volume of influence representing an intensity profile associated with energy delivered during the neuromodulation for a given center point associated with the optimal location;

acquiring a fourth image, representing activity of the brain, from the one of the first imaging system, the second imaging system, and a third imaging system after applying the neuromodulation at the optimal location a second time; and revising the connection weight for each of the set of locations for the given voxel according to the third image and the fourth image.

3. The method of claim 1, wherein determining the first utility value for each of the plurality of voxels comprises registering a portion of the first image representing the region of interest to a histology-based atlas having assigned values for the first utility value for each of a plurality of locations within the histology-based atlas.

4. The method of claim 3, wherein the assigned values within the histology-based atlas represented expected concentrations of excitatory neurons within the region of interest.

5. The method of claim 3, wherein the assigned values within the histology-based atlas represented expected concentrations of inhibitory neurons within the region of interest.

6. The method of claim 3, further comprising:

acquiring a third image, representing activity of the brain, from one of the first imaging system, the second imaging system, and a third imaging system after applying the neuromodulation at the optimal location, the applied neuromodulation having a volume of influence representing an intensity profile associated with energy delivered during neuromodulation for a given center point associated with the optimal location;

acquiring a fourth image, representing activity of the brain, from the one of the first imaging system, the second imaging system, and a third imaging system after applying the neuromodulation at the optimal location; and revising at least one of the assigned values for the first utility value for the plurality of locations within the histology-based atlas according to the third image and the fourth image.

7. The method of claim 1, further comprising:

acquiring a third image, representing activity of the brain, from one of the first imaging system, the second imaging system, and a third imaging system after applying the neuromodulation at the optimal location, the applied neuromodulation having a volume of influence, representing an intensity profile associated with energy delivered during neuromodulation for a given center point, associated with the optimal location;

acquiring a fourth image, representing activity of the brain, from the one of the first imaging system, the second imaging system, and a third imaging system after applying the neuromodulation at the optimal location; and revising the first utility value for at least one voxel within the volume of influence according to the third image and the fourth image.

8. The method of claim 1, wherein determining the optimal location for neuromodulation from the overall utility value for each of the plurality of voxels comprises determining the optimal location and an optimal shape for a volume of influence, representing an intensity profile associated with energy delivered during neuromodulation for a given center point, associated with the optimal location for neuromodulation from the overall utility value for each of the plurality of voxels.

9. The method of claim 1, further comprising:

measuring feedback comprising one of a physiological parameter, a cognitive parameter, a psychosocial parameter, a behavioral parameter of the patient;

determining an effectiveness of the neuromodulation according to the measured feedback; and selecting a new location within the region of interest from the overall utility value for each of the plurality of voxels if the effectiveness of the neuromodulation fails to meet a threshold value.

10. The method of claim 1, further comprising:

applying neuromodulation at the optimal location having a volume of influence representing an intensity profile associated with energy delivered during neuromodulation for a given center point;

measuring feedback comprising one of a physiological parameter, a cognitive parameter, a psychosocial parameter, a behavioral parameter of the patient;

determining an effectiveness of the neuromodulation according to the measured feedback; and revising the first utility value for at least one voxel within the volume of influence according to the determined effectiveness of the neuromodulation.

11. The method of claim 1, wherein the region of interest comprises at least a portion of the nucleus accumbens and the ventral internal capsule, and wherein determining the optimal location for neuromodulation from the overall utility value for each of the plurality of voxels comprises determining the optimal location such that a volume of influence, representing an intensity profile associated with energy delivered during neuromodulation for a given center point, associated with the optimal location has a center point that is between seven millimeters (mm) to twelve mm lateral from midline on the right and left sides of the brain, between one mm to six mm anterior to the anterior commissure (AC), and between two mm above to two mm below the AC.

12. A system comprising:

an imagining interface that receives a first image, representing a structure of the brain, from a first imaging system and a second image, representing a connectivity of the brain, from one of the first imaging system and a second imaging system;

a targeting component that determines a first utility value associated with directly modulating tissue within a region of interest for each of a plurality of voxels within the region of interest from the first image, determines a second utility value associated with indirectly modulating tissue outside of the region of interest by modulating tissue within the region of interest for each of the plurality of voxels from the second image, determines an overall utility value for each of the plurality of voxels from at least the first utility value and the second utility value, and determines an optimal location for neuromodulation from the overall utility value for each of the plurality of voxels, each of the first utility value, the second utility value, and the overall utility value representing a degree to which application of energy to the tissue represented by the voxel is desirable as one of a cost approach, in which positive values are assigned to regions for which application of energy is undesired and a utility approach in which positive values are assigned to regions for which application of energy is desirable, and the targeting component selecting a target location of the nucleus accumbens and the ventral internal capsule such that a volume of influence, representing an intensity profile associated with energy delivered during neuromodulation for a given center point, associated with the optimal location has a center point that is between seven millimeters (mm) to twelve mm lateral from midline on the right and left sides of the brain, between one mm to six mm anterior to the anterior commissure (AC), and between two mm above to two mm below the AC; and a neuromodulation system that delivers neuromodulation to the optimal location.

13. The system of claim 12, wherein the neuromodulation system is a deep brain stimulation system, the targeting component further determining at least one electrode to activate based on the overall utility value for each of the plurality of voxels.

14. The system of claim 12, wherein the neuromodulation system is a focused neuromodulation system, the targeting component further determining a number and orientation of focal points to use for excitation based on the overall utility value for each of the plurality of voxels.

15. The system of claim 12, further comprising a feedback component that measures one of a physiological parameter, a cognitive parameter, a psychosocial parameter, a behavioral parameter of the patient and determines an effectiveness of the neuromodulation according to the measured feedback, the targeting component selecting a new location within the region of interest from the overall utility value for each of the plurality of voxels if the effectiveness of the neuromodulation fails to meet a threshold value.

16. The system of claim 12, further comprising a feedback component that measures one of a physiological parameter, a cognitive parameter, a psychosocial parameter, a behavioral parameter of the patient and determines an effectiveness of the neuromodulation according to the measured feedback, the targeting component revising the first utility value for at least one voxel within the volume of influence according to the determined effectiveness of the neuromodulation.

17. The system of claim 12, the targeting component selecting the target location of the nucleus accumbens and the ventral internal capsule such that the volume of influence, representing an intensity profile associated with energy delivered during neuromodulation for a given center point, associated with the optimal location has a center point that is between seven millimeters (mm) to twelve mm lateral from midline on the right and left sides of the brain, between one mm to six mm anterior to the anterior commissure (AC), and between two mm above to two mm below the AC.

18. A method of improving neuropsychiatric function in a patient comprising:

acquiring a first image, representing a structure of a brain of the patient, from a first imaging system;

acquiring a second image, representing a connectivity of the brain, from one of the first imaging system and a second imaging system;

determining a first utility value associated with directly modulating tissue within a region of interest for each of a plurality of voxels within the region of interest from the first image;

determining a second utility value associated with indirectly modulating tissue outside of the region of interest by modulating tissue within the region of interest for each of the plurality of voxels from the second image;

determining an overall utility value for each of the plurality of voxels from at least the first utility value and the second utility value, each of first utility value, the second utility value, and the overall utility value representing a degree to which application of energy to the tissue represented by the voxel is desirable as one of a cost approach, in which positive values are assigned to regions for which application of energy is undesired and a utility approach in which positive values are assigned to regions for which application of energy is desirable; and selecting a volume of influence, representing an intensity profile associated with energy delivered during neuromodulation for a given center point, having a center point within a target region comprising the nucleus accumbens and the ventral internal capsule that is between seven millimeters (mm) to twelve mm lateral from midline on the right and left sides of the brain, between one mm to six mm anterior to the anterior commissure (AC), and between two mm above to two mm below the AC according to the overall utility value for each of the plurality of voxels; and delivering neuromodulation to the selected volume of influence.

19. The method of claim 18, wherein delivering neuromodulation to the selected volume of influence comprises delivering focused ultrasound to the selected volume of influence.

20. The method of claim 18, further comprising:

measuring feedback comprising one of a physiological parameter, a cognitive parameter, a psychosocial parameter, a behavioral parameter of the patient;

determining an effectiveness of the neuromodulation according to the measured feedback; and selecting a volume of influence having a center point within the target region if the effectiveness of the neuromodulation fails to meet a threshold value.

21. A method for targeting neuromodulation in a brain of a patient for one of improving, diagnosing, and managing a neuropsychiatric function, the method comprising:

acquiring a first image, representing a structure of the brain, from a first imaging system;

acquiring a second image, representing a connectivity of the brain, from one of the first imaging system and a second imaging system;

determining a first utility value associated with directly modulating tissue within a region of interest for each of a plurality of voxels within the region of interest from the first image;

determining a second utility value associated with indirectly modulating tissue outside of the region of interest by modulating tissue within the region of interest for each of the plurality of voxels from the second image;

determining an overall utility value for each of the plurality of voxels from at least the first utility value and the second utility value, each of first utility value, the second utility value, and the overall utility value representing a degree to which application of energy to the tissue represented by the voxel is desirable as one of a cost approach, in which positive values are assigned to regions for which application of energy is undesired and a utility approach in which positive values are assigned to regions for which application of energy is desirable;

determining an optimal location for neuromodulation from the overall utility value for each of the plurality of voxels acquiring a third image, representing activity of the brain, from one of the first imaging system, the second imaging system, and a third imaging system after applying the neuromodulation at the optimal location, applied neuromodulation having a volume of influence associated with the optimal location;

acquiring a fourth image, representing activity of the brain, from the one of the first imaging system, the second imaging system, and a third imaging system after applying the neuromodulation at the optimal location; and revising at least one of the assigned values for the first utility value for the plurality of locations within the histology-based atlas according to the third image and the fourth image.

*   *   *   *   *